United States Patent
Kamba et al.

(10) Patent No.: US 8,304,732 B2
(45) Date of Patent: Nov. 6, 2012

(54) METHOD OF MEASURING CHARACTERISTICS OF SPECIMEN AND FLAT-PLATE PERIODIC STRUCTURE

(75) Inventors: Seiji Kamba, Nagaokakyo (JP); Kazuhiro Takigawa, Nagaokakyo (JP); Takashi Kondo, Nagaokakyo (JP); Koji Tanaka, Nagaokakyo (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 0 days.

(21) Appl. No.: 13/405,651

(22) Filed: Feb. 27, 2012

(65) Prior Publication Data
US 2012/0153159 A1 Jun. 21, 2012

Related U.S. Application Data

(63) Continuation of application No. PCT/JP2010/063186, filed on Aug. 4, 2010.

(30) Foreign Application Priority Data

Sep. 3, 2009 (JP) ................................. 2009-203824

(51) Int. Cl.
*G01J 5/02* (2006.01)
(52) U.S. Cl. .................................................. 250/341.3
(58) Field of Classification Search .... 250/341.1–341.8, 250/338.1–338.5
See application file for complete search history.

(56) References Cited

U.S. PATENT DOCUMENTS

| 7,649,633 | B2 | 1/2010 | Kawate |
| 2003/0016358 | A1 | 1/2003 | Nagashima et al. |
| 2007/0252992 | A1 | 11/2007 | Itsuji |
| 2010/0025586 | A1 | 2/2010 | Ogawa et al. |
| 2010/0219343 | A1 | 9/2010 | Reid et al. |

FOREIGN PATENT DOCUMENTS

| JP | 2004-117703 A | 4/2004 |
| JP | 2005-129732 A | 5/2005 |
| JP | 2005-156188 A | 6/2005 |
| JP | 2006-344679 A | 12/2006 |
| JP | 2007-163181 A | 6/2007 |
| JP | 2007-298357 A | 11/2007 |
| JP | 2008-185552 A | 8/2008 |

OTHER PUBLICATIONS

El-Sabbagh et al., "Topological optimization of periodic Mindlin plates," 2008, Finite Elements in Analysis and Design, vol. 44, pp. 439-449.*

(Continued)

*Primary Examiner* — Kiho Kim
(74) *Attorney, Agent, or Firm* — Dickstein Shapiro LLP

(57) ABSTRACT

A measuring method that includes holding a specimen to be measured on a flat-plate periodic structure, applying a linearly-polarized electromagnetic wave to the flat-plate periodic structure, detecting the electromagnetic wave scattered forward or backward by the flat-plate periodic structure, and measuring characteristics of the specimen on the basis of a phenomenon that a dip waveform appearing in a frequency characteristic of the forward-scattered electromagnetic wave or a peak waveform appearing in a frequency characteristic of the backward-scattered electromagnetic wave is changed with the presence of the specimen. The flat-plate periodic structure is a flat-plate structure in which at least two voids penetrating through the structure in a direction perpendicular to a principal surface thereof are periodically arrayed in at least one direction on the principal surface, and the electromagnetic wave is applied to the principal surface of the flat-plate periodic structure from the direction perpendicular to the principal surface.

18 Claims, 26 Drawing Sheets

OTHER PUBLICATIONS

Hagiyuki et al. "Development and Applications of Meta-materials in Terahertz Band.,"Oyu Buturi (Monthly Pub. of the Japan Society of Applied Physics), Jun. 10, 2009, vol. 78, No. 6, pp. 511-517.
PCT/JP2010/063186 Written Opinion dated Jun. 9, 2010.
PCT/JP2010/060038 Written Opinion dated Jun. 9, 2010.
Miyamaru et al.; "Large polarization change in two-dimensional metallic photonic crystals in subterahertz region"; Applied Physics Letters, vol. 82, No. 16, Apr. 21, 2003, pp. 2568-2570.

* cited by examiner

METHOD OF MEASURING CHARACTERISTICS OF SPECIMEN AND FLAT-PLATE PERIODIC STRUCTURE

CROSS REFERENCE TO RELATED APPLICATIONS

The present application is a continuation of International application No. PCT/JP2010/063186, filed Aug. 4, 2010, which claims priority to Japanese Patent Application No. 2009-203824, filed Sep. 3, 2009, the entire contents of each of which are incorporated herein by reference.

FIELD OF THE INVENTION

The present invention relates to a method of holding a specimen to be measured on a flat-plate periodic structure, applying an electromagnetic wave to the flat-plate periodic structure on which the specimen is held, and detecting the scattered electromagnetic wave, thereby measuring characteristics of the specimen. The present invention also relates to the flat-plate periodic structure for use in the above-described method and to the flat-plate periodic structure used as an electromagnetic filter.

BACKGROUND OF THE INVENTION

Hitherto, characteristics of substances have been analyzed by a measuring method of holding a specimen on a void-arrayed structure, applying an electromagnetic wave to the void-arrayed structure on which the specimen is held, and analyzing a transmittance spectrum of the electromagnetic wave, thereby detecting characteristics of the specimen. More specifically, there is, for example, a method of applying a terahertz wave to a specimen, e.g., a protein, attached to a metal mesh film, and analyzing a transmittance spectrum of the terahertz wave.

As such a related-art transmittance spectrum analyzing method using the electromagnetic wave, Japanese Unexamined Patent Application Publication No. 2008-185552 (Patent Literature (PTL) 1) discloses a measuring method of applying an electromagnetic wave to a void-arrayed structure (e.g., a metal mesh), which has a void region where a specimen is held, in an oblique direction with respect to a direction perpendicular to a principal surface of the void-arrayed structure, measuring the electromagnetic wave having transmitted through the void-arrayed structure, and detecting characteristics of the specimen on the basis of a phenomenon that the position of a dip waveform appearing in a frequency characteristic of a measured value is shifted with the presence of the specimen.

PTL 1: Japanese Unexamined Patent Application Publication No. 2008-185552

SUMMARY OF THE INVENTION

In the related-art measuring method in which the electromagnetic wave is incident on the void-arrayed structure obliquely with respect to the principal surface of the void-arrayed structure, a problem resides in that because the dip waveform, for example, appearing in the frequency characteristic is broad, it is difficult to detect the shift of the position of the dip waveform, for example, when the amount of the specimen is very small.

Another problem with the related art described above is that, because a variation in the incidence angle of the electromagnetic wave causes a variation in the dip waveform, for example, a difficulty also arises in carrying out the detection when the amount of the specimen is very small.

In view of the above-described state of the art, an object of the present invention is to provide a method of measuring characteristics of a specimen with improved measurement sensitivity and higher reproducibility, and a flat-plate periodic structure for use in the measuring method.

The present invention provides a measuring method comprising the steps of holding a specimen to be measured on a flat-plate periodic structure;
applying a linearly-polarized electromagnetic wave to the flat-plate periodic structure;
detecting the electromagnetic wave scattered forward or backward by the flat-plate periodic structure; and
measuring characteristics of the specimen on the basis of a phenomenon that a dip waveform appearing in a frequency characteristic of the forward-scattered electromagnetic wave or a peak waveform appearing in a frequency characteristic of the backward-scattered electromagnetic wave is changed with the presence of the specimen,
wherein the flat-plate periodic structure is a flat-plate structure in which at least two voids penetrating through the structure in a direction perpendicular to a principal surface thereof are periodically arrayed in at least one direction on the principal surface, and
the electromagnetic wave is applied to the principal surface of the flat-plate periodic structure from the direction perpendicular to the principal surface.

Preferably, the dip waveform appearing in the frequency characteristic of the forward-scattered electromagnetic wave or the peak waveform appearing in the frequency characteristic of the backward-scattered electromagnetic wave is generated by TE11 mode-like resonance in the flat-plate periodic structure.

Preferably, the TE11 mode-like resonance is TE110 mode-like resonance.

Preferably, the void has a shape that is not mirror-symmetric with respect to an imaginary plane perpendicular to a polarizing direction of the electromagnetic wave.

Preferably, a projection or a cutout is provided in a portion defining the void of the periodic structure.

Preferably, the projection is provided at a position in the portion defining the void of the periodic structure at which electric field intensity is relatively intensified when the TE11 mode-like resonance is produced, or the cutout is provided at a position in the portion defining the void of the periodic structure at which the electric field intensity is relatively weakened.

Preferably, a shape of the void as viewed in the direction perpendicular to the principal surface of the periodic structure is trapezoidal, convex, concave, polygonal, or star-like.

Preferably, a substance differing from the periodic structure is attached to only a partial region of the portion defining the void of the periodic structure.

Preferably, the substance differing from the periodic structure is selectively held at a position in the portion defining the void of the periodic structure at which electric field intensity is relatively intensified when the TE11 mode-like resonance is produced.

Preferably, the specimen is held in only a partial region of the portion defining the void of the periodic structure.

Preferably, the specimen is selectively held at the position in the portion defining the void of the periodic structure at which the electric field intensity is relatively intensified when the TE11 mode-like resonance is produced.

Further, the present invention provides a flat-plate periodic structure for use in the above-described measuring method, wherein at least two voids penetrating through the flat-plate periodic structure in a direction perpendicular to a principal surface thereof are periodically arrayed in at least one direction on the principal surface of the flat-plate periodic structure, and in a state that the flat-plate periodic structure is arranged when used in the above-described measuring method, the void has a shape that is not mirror-symmetric with respect to an imaginary plane perpendicular to a polarizing direction of the electromagnetic wave.

Still further, the present invention provides a flat-plate periodic structure used as a filter for a linearly polarized electromagnetic wave, wherein at least two voids penetrating through the flat-plate periodic structure in a direction perpendicular to a principal surface thereof are periodically arrayed in at least one direction on the principal surface of the flat-plate periodic structure, and in a state that the principal surface of the periodic structure is arranged perpendicularly to a propagating direction of the electromagnetic wave when the periodic structure is used as the filter for the electromagnetic wave, the void has a shape that is not mirror-symmetric with respect to an imaginary plane perpendicular to a polarizing direction of the electromagnetic wave.

According to the present invention, since the shape of the void of the flat-plate periodic structure used in measurement is not mirror-symmetric with respect to the imaginary plane perpendicular to the polarizing direction of the electromagnetic wave when the electromagnetic wave is applied to the principal surface of the flat-plate periodic from the direction perpendicular to the principal surface, the measurement of the specimen can be performed even with the electromagnetic wave applied to the principal surface of the flat-plate periodic structure from the direction perpendicular to the principal surface. Therefore, a variation in the measurement caused by a variation in the incidence angle of the electromagnetic wave is reduced and sensitivity in measuring the specimen is increased.

Further, when the void of the flat-plate periodic structure used in the present invention is configured such that the dip waveform appearing in the frequency characteristic of the forward-scattered electromagnetic wave or the peak waveform appearing in the frequency characteristic of the backward-scattered electromagnetic wave is generated by the TE11 mode-like resonance in the flat-plate periodic structure, the dip waveform or the peak waveform is obtained in a narrower band width and a sharper shape than those obtained when the electromagnetic wave is applied to the related-art flat-plate periodic structure from an oblique direction. Hence, the method of measuring the characteristics of the specimen with higher measurement sensitivity can be provided.

BRIEF DESCRIPTION OF THE DRAWINGS

FIG. 1($b$) is a perspective view illustrating a void in one example of a flat-plate periodic structure of the related art.

FIG. 3($b$) depicts a frequency characteristic of transmittance [dB] with the related-art periodic structure 9 illustrated in FIG. 1($b$).

FIG. 4($b$) depicts a frequency characteristic of reflectance [dB] with the related-art periodic structure 9 illustrated in FIG. 1($b$).

FIG. 5($b$) depicts a diagram of resonance electric field vectors in the void of the related-art periodic structure 9, illustrated in FIG. 1($b$), at a frequency of 980 GHz.

FIG. 6($b$) depicts the calculation result of a frequency characteristic of transmittance [dB] with the periodic structure illustrated in FIG. 6($a$).

FIG. 7($b$) depicts the calculation result of a frequency characteristic of transmittance [dB] with the periodic structure illustrated in FIG. 7($a$).

FIG. 8($b$) depicts the calculation result of a frequency characteristic of transmittance [dB] with the periodic structure illustrated in FIG. 8($a$).

FIG. 9($b$) depicts the calculation result of a frequency characteristic of transmittance [dB] with the periodic structure illustrated in FIG. 9($a$).

FIG. 10($b$) depicts the calculation result of a frequency characteristic of transmittance [dB] with the periodic structure illustrated in FIG. 10($a$).

FIG. 11($b$) depicts the calculation result of a frequency characteristic of transmittance [dB] with the periodic structure illustrated in FIG. 11($a$).

FIG. 18($b$) depicts the calculation result of a frequency characteristic of transmittance [dB] with the periodic structure illustrated in FIG. 18($a$).

DETAILED DESCRIPTION OF THE PREFERRED EMBODIMENTS

Figure 12:
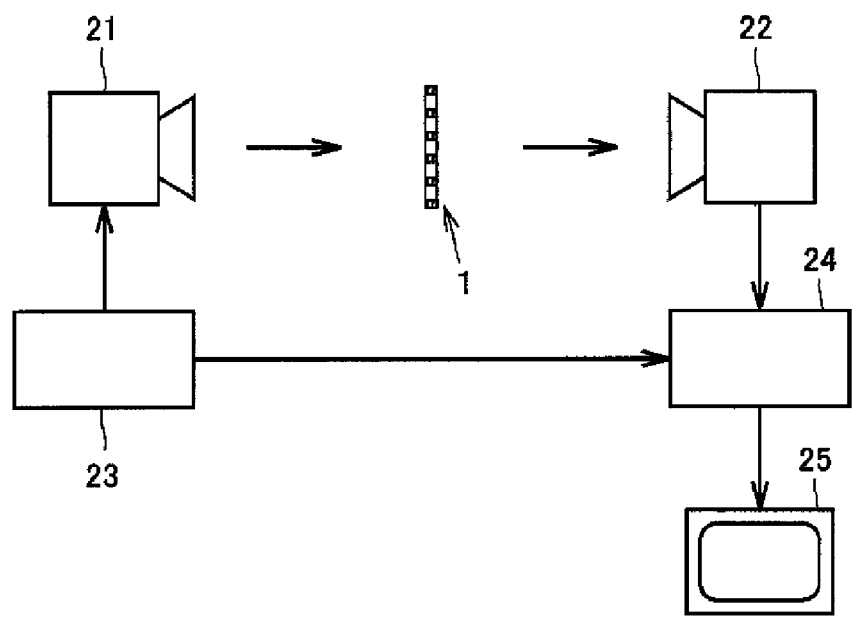
FIG. 12 is a schematic view to explain the gist of the measuring method according to the present invention.

The gist of one example of a measuring method according to the present invention will be described with reference to FIG. 12. FIG. 12 is a schematic view illustrating the overall configuration of a measuring device 2, which is used in the measuring method according to the present invention, and the layout of a flat-plate periodic structure 1 in the measuring device 2. As illustrated in FIG. 12, the measuring device 2 includes an irradiation unit 21 for generating and emitting an electromagnetic wave, and a detection unit 22 for detecting the electromagnetic wave that has transmitted through the flat-plate periodic structure 1. Further, the measuring device 2 includes an irradiation control unit 23 for controlling the operation of the irradiation unit 21, an analysis processing unit 24 for analyzing the result detected by the detection unit 22, and a display unit 25 for displaying the result analyzed by the analysis processing unit 24. The irradiation control unit 23 may be connected to the analysis processing unit 24 as well for the purpose of synchronizing the timing of the detection.

FIG. 12 illustrates the case where scattering occurs as transmission, i.e., the case of measuring a transmittance of the electromagnetic wave. The term "scattering" used in the present invention implies a wide-sense concept including transmission as one form of forward scattering, reflection as one form of backward scattering, etc. Preferably, the term "scattering" implies transmission and reflection. More preferably, the term "scattering" implies transmission in the 0-th order direction and reflection in the 0-th order direction.

In general, given that a lattice interval of a grating (i.e., a void interval in this Description) is d, an incidence angle is i, a diffraction angle is θ, and a wavelength is λ, a spectrum diffracted by the grating can be expressed by:

$$d(\sin i - \sin \theta) = n\lambda \tag{1}$$

The "0-th order" in the term "0-th order direction" implies the case where n in the above formula (1) is 0. Because d and λ cannot take 0, n=0 holds only when sin i−sin θ=0 is satisfied. Thus, the "0-th order direction" implies the direction in which the incidence angle and the diffraction angle are equal to each other, i.e., in which a propagating direction of the electromagnetic wave is not changed.

In the above-described measuring device 2, the irradiation unit 21 generates and emits the electromagnetic wave under control of the irradiation control unit 23. The electromagnetic wave emitted from the irradiation unit 21 is applied to the flat-plate periodic structure 1, and the electromagnetic wave having transmitted through the flat-plate periodic structure 1 is detected by the detection unit 22. The electromagnetic wave detected by the detection unit 22 is transferred in the form of an electric signal to the analysis processing unit 24 and is displayed on the display unit 25 in the visually recognizable form as a frequency characteristic of transmittance (i.e., a transmittance spectrum).

The electromagnetic wave used in the measuring method according to the present invention is not limited to particular one insofar as it can cause scattering depending on a specific structure of the flat-plate periodic structure 1. In practice, the electromagnetic wave may be any of an electric wave, an infrared ray, a visible ray, an ultraviolet ray, an X-ray, and a gamma ray, and its frequency is also not limited to particular one. However, the electromagnetic wave is preferably a terahertz wave having frequency of 1 GHz to 1 PHz, more preferably 20 GHz to 120 THz. Further, the electromagnetic wave used in the present invention is usually a linearly polarized electromagnetic wave. Practical examples of the electromagnetic wave include a terahertz wave that is generated with the optical rectification effect of an electro-optical crystal, e.g., ZnTe, by using a short optical pulse laser as a light source, an infrared ray radiated from a high-pressure mercury lamp or a ceramic lamp, visible light emitted from a semiconductor laser, and an electromagnetic wave radiated from a photoconductive antenna.

In the present invention, the expression "measuring the characteristics of the specimen" implies, e.g., quantitative measurement of a compound as the specimen and qualitative measurement of a dielectric constant and other properties thereof. There are, for example, the case of measuring a minute content of the specimen in, e.g., a solution and the case of identifying the specimen. More specifically, one exemplary method includes the steps of immersing the flat-plate periodic structure in a solution in which the specimen is dissolved, washing a solvent and the extra specimen after the specimen has been attached to the surface of the flat-plate periodic structure, drying the flat-plate periodic structure, and measuring characteristics of the specimen by using a measuring device such as described above. Another exemplary method includes the steps of attaching the specimen to a sheet-like base material made of, e.g., a polymer, holding the flat-plate periodic structure in close contact with the sheet-like base material, and measuring characteristics of the specimen by using a measuring device such as described above.

The flat-plate periodic structure used in the present invention is a flat-plate structure in which at least two voids penetrating through the flat-plate structure in a direction perpendicular to a principal surface thereof are periodically arrayed in at least one direction on the principal surface of the flat-plate periodic structure. Here, the voids may be all periodically arrayed. As an alternative, some of the voids may be periodically arrayed and the other voids may be aperiodically arrayed insofar as the advantageous effects of the present invention are not impaired.

Preferably, the flat-plate periodic structure is a quasi-periodic structure or a periodic structure. The term "quasi-periodic structure" implies a structure in which translational symmetry is not held, but the array is orderly kept. Examples of the quasi-periodic structure include a Fibonacci structure as a one-dimensional quasi-periodic structure, and a Penrose structure as a two-dimensional quasi-periodic structure. The term "periodic structure" implies a structure having spatial symmetry such as represented by translational symmetry. The periodic structure is classified into one-dimensional periodic structure, a two-dimensional periodic structure, and a three-dimensional periodic structure depending on the dimension of the symmetry. The one-dimensional periodic structure is, for example, a wire grid structure or a one-dimensional grating. The two-dimensional periodic structure is, for example, a mesh filter or a two-dimensional grating. Of those periodic structures, the two-dimensional periodic structure is preferably employed. In practice, a structure including voids regularly arrayed in at least two directions is employed as one example.

Figure 13A:
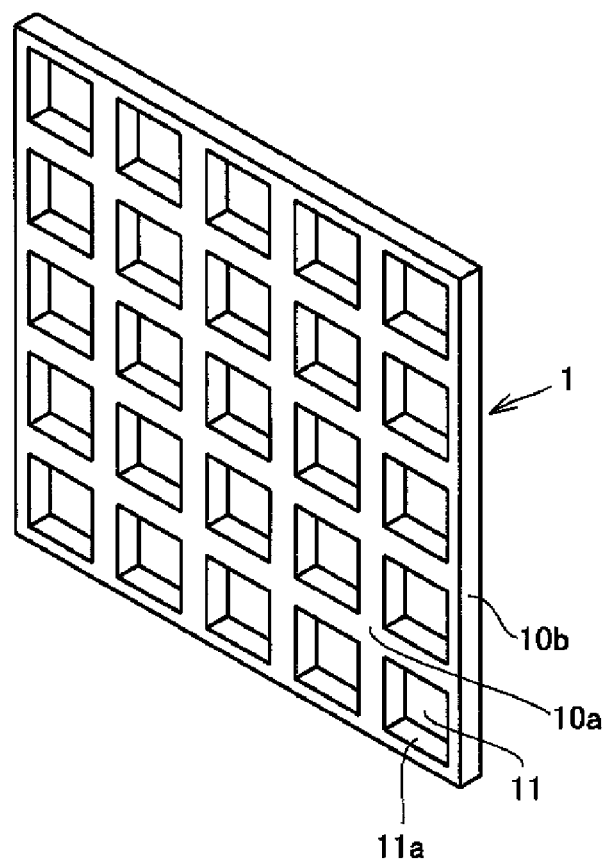
FIGS. 13($a$) and 13($b$) are schematic views to explain a lattice structure of the flat-plate periodic structure.
Figure 13B:
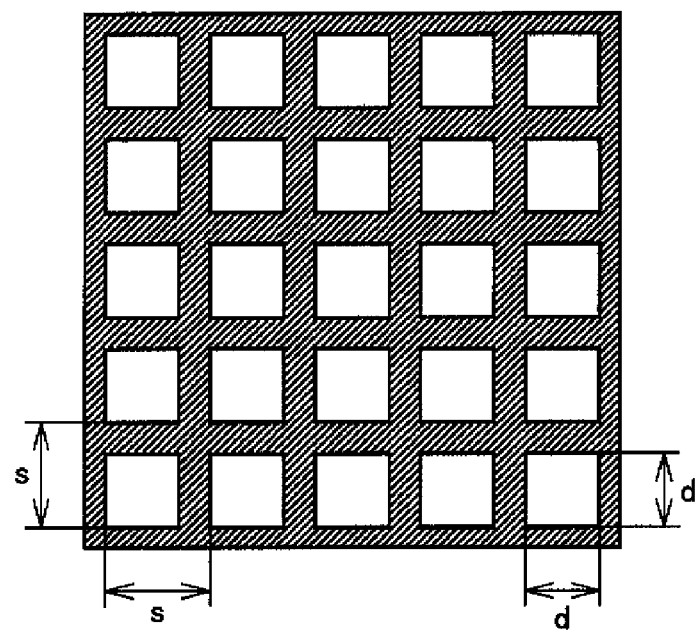

One example of the two-dimensional periodic structure is, e.g., a flat-plate structure (lattice structure) in which the voids are arrayed in a matrix pattern at constant intervals, as illustrated in FIG. 13(a). The flat-plate periodic structure 1, illustrated in FIG. 13(a), is a structure in which voids 11, each having a square shape as viewed from the front side of a principal surface 10a, are formed at equal intervals in a vertical direction and a horizontal direction in the drawing. It is to be noted that FIGS. 13(a) and 13(b) are intended just for explanation and a projection, a cutout, or the like provided in association with the void of the flat-plate periodic structure according to the present invention is omitted from the drawings.

The shape of the void formed in the flat-plate periodic structure is preferably such a shape as producing TE11 mode-like resonance upon irradiation with the electromagnetic wave when each void is regarded as a waveguide. Herein, the term "TE11 mode-like resonance" includes resonance in the TE11 mode and resonance in a mode analogous to the TE11 mode. The void having such a shape as producing the TE11 mode-like resonance is advantageous in that a sharp dip waveform can be obtained in a frequency characteristic of the forward-scattered electromagnetic wave, or that a sharp peak waveform can be obtained in a frequency characteristic of the backward-scattered electromagnetic wave.

Herein, the term "dip waveform" implies a waveform in a valley-shaped (downward-convex) portion, which partly appears in a frequency characteristic (e.g., a transmittance spectrum) with the flat-plate periodic structure in a frequency range where a ratio of the detected electromagnetic wave to the applied electromagnetic wave (e.g., a transmittance of the electromagnetic wave) is relatively increased. Also, the term "peak waveform" implies a waveform in a mountain-shaped (upward-convex) portion, which partly appears in a frequency characteristic (e.g., a reflectance spectrum) with the flat-plate periodic structure in a frequency range where a ratio of the detected electromagnetic wave to the applied electromagnetic wave (e.g., a reflectance of the electromagnetic wave) is relatively reduced.

The void shape producing the TE11 mode-like resonance is preferably, for example, a shape that is not mirror-symmetric with respect to an imaginary plane perpendicular to the polarizing direction of the electromagnetic wave in a state that the structure is arranged when irradiated with the electromagnetic wave. Practical examples of the void shape include a trapezoidal shape, a convex shape (i.e., a shape obtained by centrally projecting one side of a rectangle), a concave shape (i.e., a shape obtained by centrally recessing one side of a rectangle), or a star-like shape, as viewed in the direction perpendicular to the principal surface of the periodic structure. As a polygonal shape of the void, one of polygonal shapes other than the shapes of regular polygons or one of the shapes of regular polygons having odd angles (e.g., a regular triangle and a regular pentagon) is preferably used. Of those examples, the convex shape or the trapezoidal shape is preferable. From the viewpoint of easiness in machining, the trapezoidal shape is more preferable. When the flat-plate periodic structure has the triangular void, for example, the void shape becomes mirror-symmetric with respect to the imaginary plane perpendicular to the polarizing direction of the electromagnetic wave in some cases depending on the polarizing direction of the electromagnetic wave applied. Even in such a case, however, the measuring method according to the present invention can be practiced by adjusting the polarizing direction of the electromagnetic wave such that the void shape will not become mirror-symmetric with respect to the imaginary plane.

Further, in order that the void has the shape not mirror-symmetric with respect to the imaginary plane perpendicular to the polarizing direction of the electromagnetic wave, the periodic structure preferably includes a projection or a cutout in its portion forming the void. Herein, the projection is preferably provided at a position in the flat-plate periodic structure where the electric field intensity is relatively intensified (i.e., the magnitude of an electric field vector is relatively increased) when the TE11 mode-like resonance is produced. Also, the cutout is preferably provided at a position in the flat-plate periodic structure where the electric field intensity is relatively weakened (i.e., the magnitude of an electric field vector is relatively reduced) when the TE11 mode-like resonance is produced. Providing the projection or the cutout at such a position is advantageous in that a sharp dip waveform can be obtained in a frequency characteristic of the forward-scattered electromagnetic wave, or that a sharp peak waveform can be obtained in a frequency characteristic of the backward-scattered electromagnetic wave.

As an alternative, two voids divided by the above-mentioned imaginary plane may be caused to have different shapes by attaching a substance to a portion of the flat-plate periodic structure, which portion forms the void.

Additionally, in order that the dip waveform appearing in the frequency characteristic of the forward-scattered electromagnetic wave or the peak waveform appearing in the frequency characteristic of the backward-scattered electromagnetic wave is generated due to the TE11 mode-like resonance in the flat-plate periodic structure, it is not always required that the void formed in the flat-plate periodic structure has the shape producing the TE11 mode-like resonance upon irradiation with the electromagnetic wave when each void is regarded as a waveguide.

For example, by selectively attaching a substance (e.g., a dielectric), which differs from the material of the periodic structure, to only a portion of the surface forming the void in the periodic structure, the dip waveform appearing in the frequency characteristic of the forward-scattered electromagnetic wave or the peak waveform appearing in the frequency characteristic of the backward-scattered electromagnetic wave can also be generated with the TE11 mode-like resonance in the flat-plate periodic structure.

In that case, preferably, the substance differing from the material of the periodic structure is selectively attached to the position in the flat-plate periodic structure where the electric field intensity is relatively intensified when the TE11 mode-like resonance is produced. By attaching the substance differing from the material of the periodic structure to such a position, the sharp dip waveform can be obtained in the frequency characteristic of the forward-scattered electromagnetic wave, or the sharp peak waveform can be obtained in the frequency characteristic of the backward-scattered electromagnetic wave.

Further, by covering a portion of the surface forming the void in the periodic structure with, e.g., a substance having a high associativity with the specimen such that the specimen is selectively held on the periodic structure, the dip waveform appearing in the frequency characteristic of the forward-scattered electromagnetic wave or the peak waveform appearing in the frequency characteristic of the backward-scattered electromagnetic wave can be generated with the TE11 mode-like resonance in the flat-plate periodic structure.

In that case, preferably, the specimen is selectively attached to the position in the flat-plate periodic structure where the electric field intensity is relatively intensified when the TE11 mode-like resonance is produced. By attaching the substance differing from the material of the periodic structure to such a position, the sharp dip waveform can be obtained in the frequency characteristic of the forward-scattered electromagnetic wave, or the sharp peak waveform can be obtained in the frequency characteristic of the backward-scattered electromagnetic wave.

The TE11 mode-like resonance produced with the above-described periodic structure used in the present invention is usually the TE110 mode-like resonance.

The size of the void is designed, as appropriate, depending on the measuring method, the material characteristics of the flat-plate periodic structure, the frequency of the electromagnetic wave used, etc. It is hence difficult to generalize the range of the void size. However, when the forward-scattered electromagnetic wave is detected, it is preferable in the flat-plate periodic structure 1, in which the voids are regularly arrayed in the vertical and horizontal directions as illustrated in FIG. 13($a$), that the lattice interval of the voids, denoted by s in FIG. 13($b$), is not shorter than $1/10$ and not longer than 10 times the wavelength of the electromagnetic wave used in the measurement. If the lattice interval s of the voids is outside that range, the electromagnetic wave may be less apt to scatter in some cases. Further, it is preferable that the opening size of the void, denoted by d in FIG. 13($b$), is not smaller than $1/10$ and not larger than 10 times the wavelength of the electromagnetic wave used in the measurement. If the opening size d of the void is outside that range, the intensity of the transmitted (forward-scattered) electromagnetic wave may be so weakened as to cause a difficulty in detecting the signal in some cases.

Further, the thickness of the flat-plate periodic structure is designed, as appropriate, depending on the measuring method, the material characteristics of the flat-plate periodic structure, the frequency of the electromagnetic wave used, etc. It is hence difficult to generalize the range of thickness of the flat-plate periodic structure. However, when the (forward-scattered) electromagnetic wave is detected, the thickness of the flat-plate periodic structure is preferably not larger than several times the wavelength of the electromagnetic wave used in the measurement. If the structure thickness exceeds that range, the intensity of the forward-scattered electromagnetic wave may be so weakened as to cause a difficulty in detecting the signal in some cases.

In the present invention, the specimen can be held on the flat-plate periodic structure by optionally using various known methods. For example, the specimen may be directly attached to the flat-plate periodic structure or may be attached to the flat-plate periodic structure with, e.g., a support film interposed therebetween. However, the specimen is preferably directly attached to the surface of the flat-plate periodic structure from the viewpoint of improving measurement sensitivity and reducing variations in the measurement, thereby performing the measurement with higher reproducibility.

Direct attachment of the specimen to the flat-plate periodic structure includes not only the case where chemical bonding, for example, is directly formed between the surface of the flat-plate periodic structure and the specimen, but also the case where, by using a flat-plate periodic structure having the surface to which a host molecule is bonded in advance, the specimen is bonded to the host molecule. Examples of the chemical bonding include covalent bonding (e.g., covalent bonding between a metal and a thiol group), Van der Waals bonding, ionic bonding, metal bonding, and hydrogen bonding. Of those examples, the covalent bonding is preferable. The term "host molecule" implies a molecule capable of being bonded specifically to the specimen. Combinations of the host molecule and the specimen are, for example, an antigen and an antibody, a sugar chain and a protein, a lipid and a protein, a low-molecule compound (ligand) and a protein, a protein and a protein, as well as a single strand DNA and a single strand DNA.

When the specimen is directly attached to the flat-plate periodic structure, it is preferable to use a flat-plate periodic structure in which at least a part of the surface of the flat-plate periodic structure is formed by a conductor. The expression "at least a part of the surface of the flat-plate periodic structure 1" implies a part of any of the principal surface 10$a$, a side surface 10$b$ of the flat-plate periodic structure, and a side surface 11$a$ of the void, which are illustrated in FIG. 13($a$).

Herein, the term "conductor" implies an object (substance) capable of conducting electricity therethrough, and it includes not only a metal, but also a semiconductor. Examples of the metal include a metal capable of being bonded to a functional group, such as a hydroxyl group, a thiol group, or a carboxyl group, of a compound containing that functional group, a metal capable of coating a functional group, such as a hydroxyl group or an amino group, on a surface of the metal, and an alloy of those metals. Practical examples of the metals are gold, silver, copper, iron, nickel, chromium, silicon, germanium, etc. Of those examples, gold, silver, copper, nickel, and chromium are preferable. Gold is more preferable. Using gold or nickel is advantageous in that, particularly when the specimen contains a thiol group (—SH group), the thiol group can be bonded to the surface of the flat-plate periodic structure. Further, using nickel is advantageous in that, particularly when the specimen contains a hydroxyl group (—OH) or a carboxyl group (—COOH), such a functional group can be bonded to the surface of the flat-plate periodic structure. Further, examples of the semiconductor include a group IV semiconductor (e.g., Si or Ge), compound semiconductors, e.g., a group II-VI semiconductor (e.g., ZnSe, CdS or ZnO), a group III-V semiconductor (e.g., GaAs, InP or GaN), a group IV compound semiconductor (e.g., SiC or SiGe), and a group I-III-VI semiconductor (e.g., $CuInSe_2$), as well as organic semiconductors.

The attachment of the specimen to the flat-plate periodic structure with, e.g., a support film interposed therebetween can be performed, for example, by a method of sticking a support film made of, e.g., a polyamide resin to the surface of the flat-plate periodic structure and attaching the specimen to the support film, or a method of using a gas-tight or liquid-tight container instead of the support film and measuring a fluid or a substance dispersed in a fluid.

With the measuring method according to the present invention, the characteristics of the specimen are measured on the basis of at least one parameter relating to the frequency characteristic, which is determined as described above, of the electromagnetic wave dispersed by the flat-plate periodic structure. The characteristics of the specimen can be measured, for example, on the basis of a phenomenon that, when the flat-plate periodic structure 1 is employed, the dip waveform appearing in the frequency characteristic of the forward-dispersed (transmitted) electromagnetic wave or the peak waveform appearing in the frequency characteristic of the backward-dispersed (reflected) electromagnetic wave is changed with the presence of the specimen.

Figure 1A:
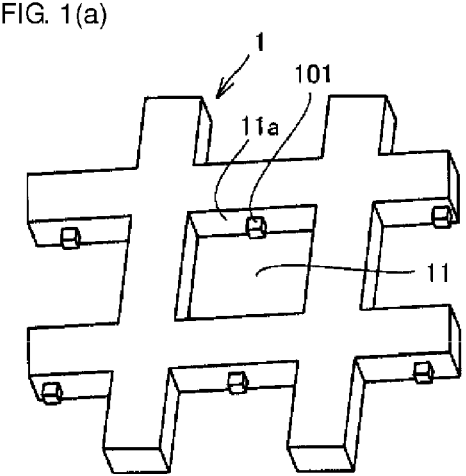
FIG. 1($a$) is a perspective view illustrating a void in one example of a flat-plate periodic structure according to the present invention.

An electromagnetic field simulation with the FDTD (Finite-difference time-domain) method was carried out, by way of example, on the flat-plate periodic structure including, as illustrated in FIG. 1(a), a projection added to its portion forming the void. The operation of the present invention is described below on the basis of the simulation result.

FIG. 1(a) is a perspective view illustrating the void of the flat-plate periodic structure 1 according to the present invention. The flat-plate periodic structure 1 illustrated in FIG. 1(a) has a structure that a projection having a cubic shape with dimensions of 20×20×20 μm is added to a side surface 91a defining a void in a related-art periodic structure 9 illustrated in FIG. 1(b).

Figure 1B:
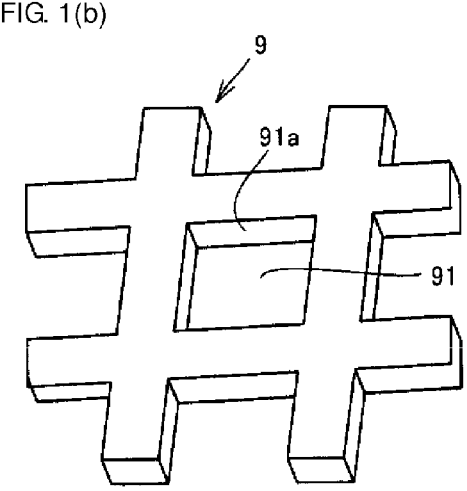

Further, FIG. 1(b) is a perspective view illustrating a void of the related-art flat-plate periodic structure 9 as a reference. The related-art periodic structure 9, illustrated in FIG. 1(b), has a structure that through-holes (voids) each having a square shape with dimensions of 180×180 μm are formed in an Au-made flat plate having a thickness of 60 μm, and the voids are periodically arrayed in the form of a regular lattice at a pitch of 254 μm.

Figure 2A:
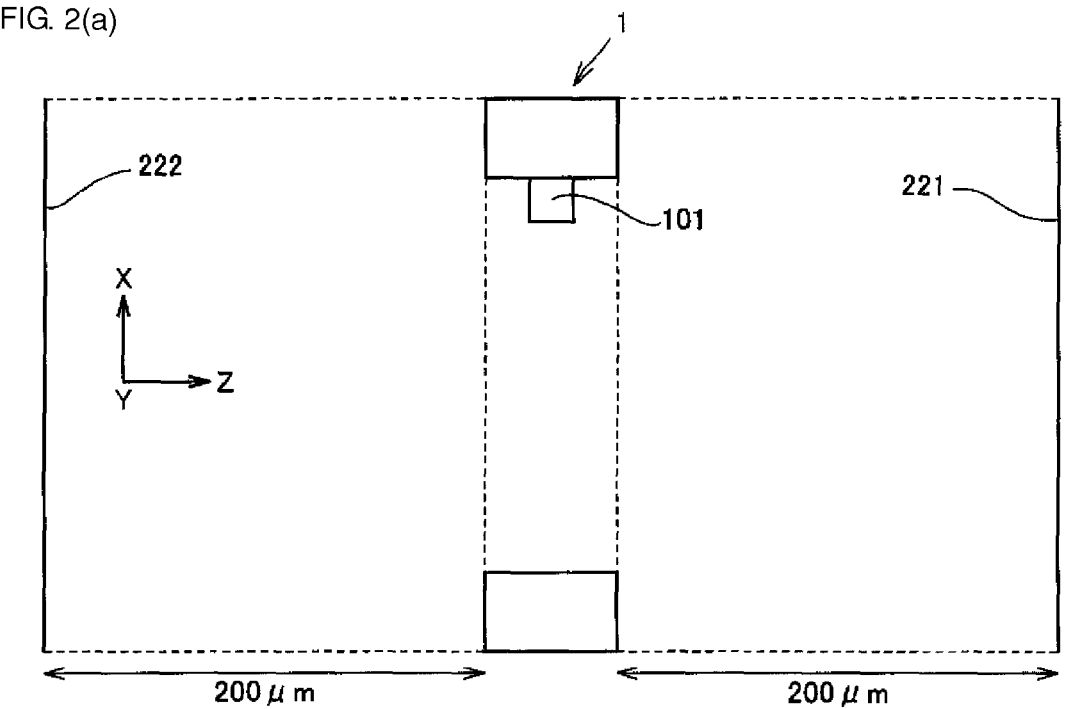
FIGS. 2($a$) and 2($b$) are illustrations to explain conditions for simulation of an electromagnetic field. Specifically, FIG. 2($a$) is a side view, and FIG. 2($b$) is a front view.
Figure 2B:
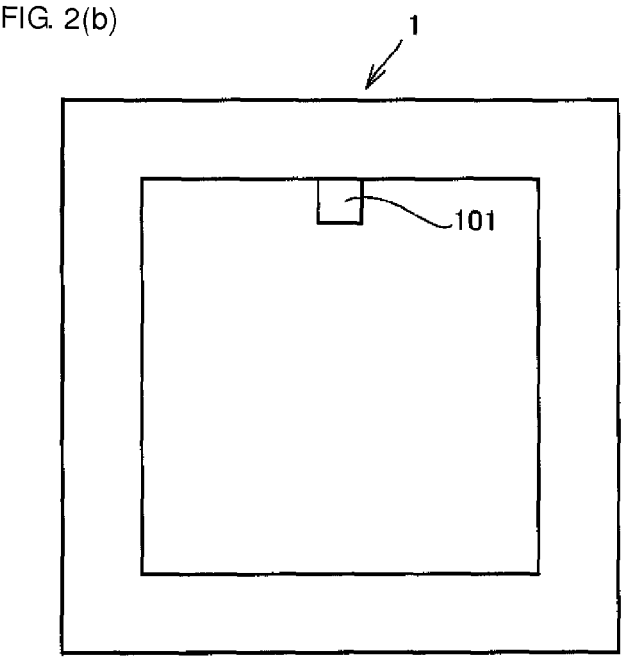

Conditions for the electromagnetic field simulation will be described below with reference to FIGS. 2(a) and 2(b). In the electromagnetic field simulation with the FDTD method, as illustrated in FIGS. 2(a) and 2(b), a principal surface of an elementary unit (254×254×60 μm) of the periodic structure 1 is set as a plane of incidence, a surface opposite to the above-mentioned principal surface is set as a detection plane, and other surfaces of the elementary unit than those surfaces are set as periodic boundaries. Further, the elementary unit is divided into unit cells with dimensions being all 5 μm in the XYZ-directions. The periodic structure is made of Au. While FIGS. 2(a) and 2(b) are explanatory views relating to the periodic structure 1 illustrated in FIG. 1(a), the same conditions as those described above are applied to the related-art periodic structure 9 as well. The electromagnetic wave is incident on the periodic structure such that a plane wave (linearly polarized wave) perpendicularly enters the principal surface of the structure, and that one side of the void, to which the projection 101 is added, and the polarization plane (electric field plane) of the incident electromagnetic wave are orthogonal to each other. In FIG. 2(a), X denotes the direction of an electric field (i.e., the polarizing direction), Y (direction perpendicular to the drawing sheet) denotes the direction of a magnetic field, and Z denotes the propagating direction of the electromagnetic wave. Further, the scattered wave from the flat-plate periodic structure is measured by detecting the forward-scattered wave (i.e., the wave having transmitted through the structure), and the transmitted electromagnetic wave is detected at a detection plane 221 disposed on the side opposite to a source of the plane wave. The distance between the periodic structure 1 and the detection plane 221 is set to 200 μm.

Figure 3A:
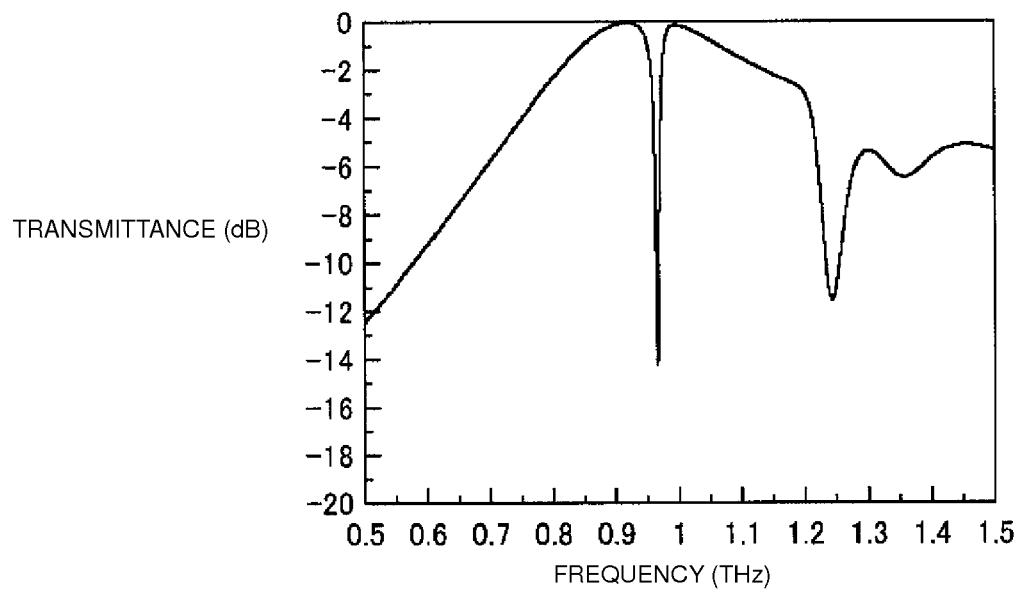
FIG. 3($a$) depicts a frequency characteristic of transmittance [dB] with the periodic structure 1 of the present invention, illustrated in FIG. 1($a$).
Figure 3B:
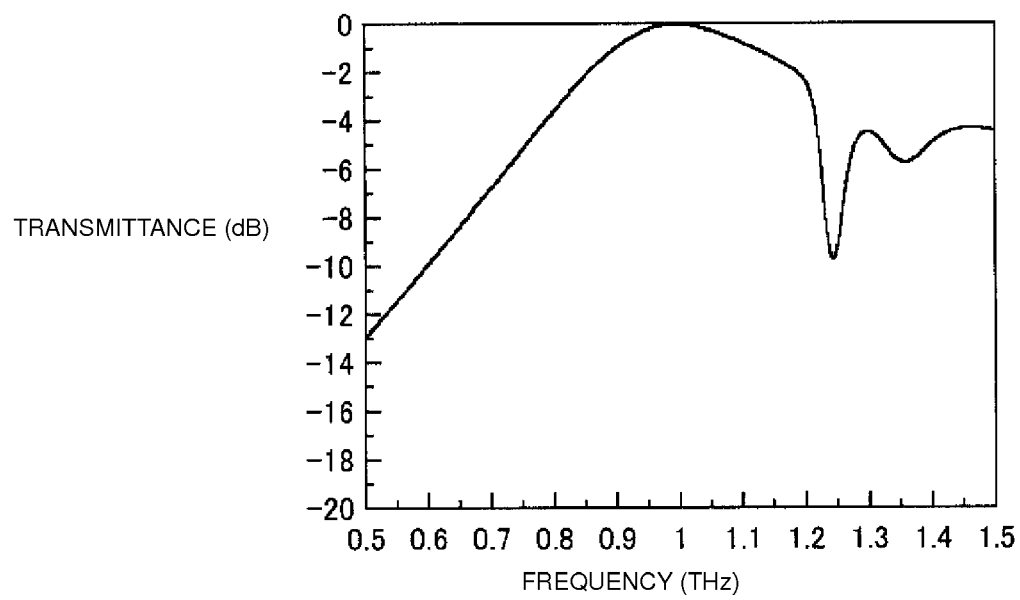

FIG. 3(a) depicts a frequency characteristic of transmittance [dB] with the periodic structure 1 of the present invention, illustrated in FIG. 1(a). FIG. 3(b) depicts a frequency characteristic of transmittance [dB] with the related-art periodic structure 9 illustrated in FIG. 1(b).

Figure 4A:
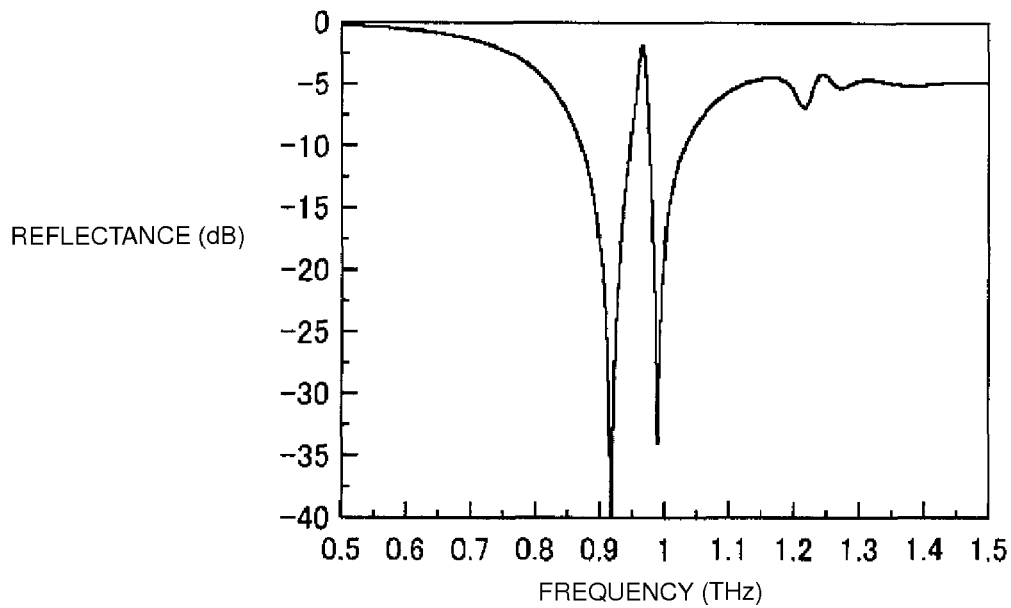
FIG. 4($a$) depicts a frequency characteristic of reflectance [dB] with the periodic structure 1 of the present invention, illustrated in FIG. 1($a$).
Figure 4B:
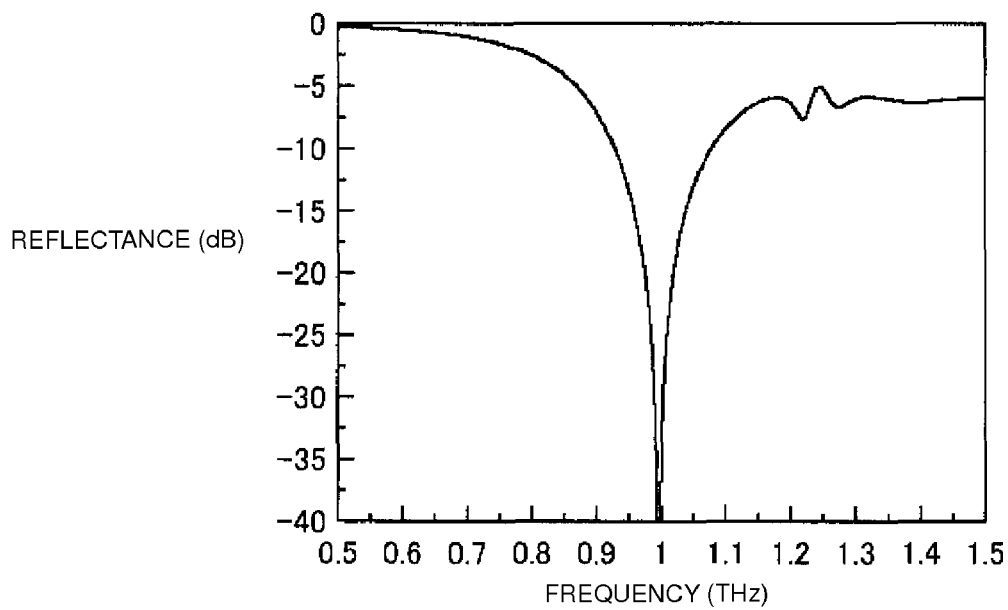

Similarly, an electromagnetic field simulation was performed on the case of detecting the backward-scattered (reflected) electromagnetic wave at a detection plane 222 disposed on the same side as the source of the plane wave. FIG. 4(a) depicts a frequency characteristic of reflectance [dB] with the periodic structure 1 of the present invention, illustrated in FIG. 1(a). FIG. 4(b) depicts a frequency characteristic of reflectance [dB] with the related-art periodic structure 9 illustrated in FIG. 1(b).

As seen from comparing FIGS. 3 and 4 with each other, the dip waveform appearing in the frequency characteristic of the forward-scattered electromagnetic wave (i.e., in the transmittance spectrum) and the peak waveform appearing in the frequency characteristic of the backward-scattered electromagnetic wave (i.e., in the reflectance spectrum) are generated at frequency near 980 GHz only in the periodic structure 1 of the present invention, illustrated in FIG. 1(a).

Figure 5A:
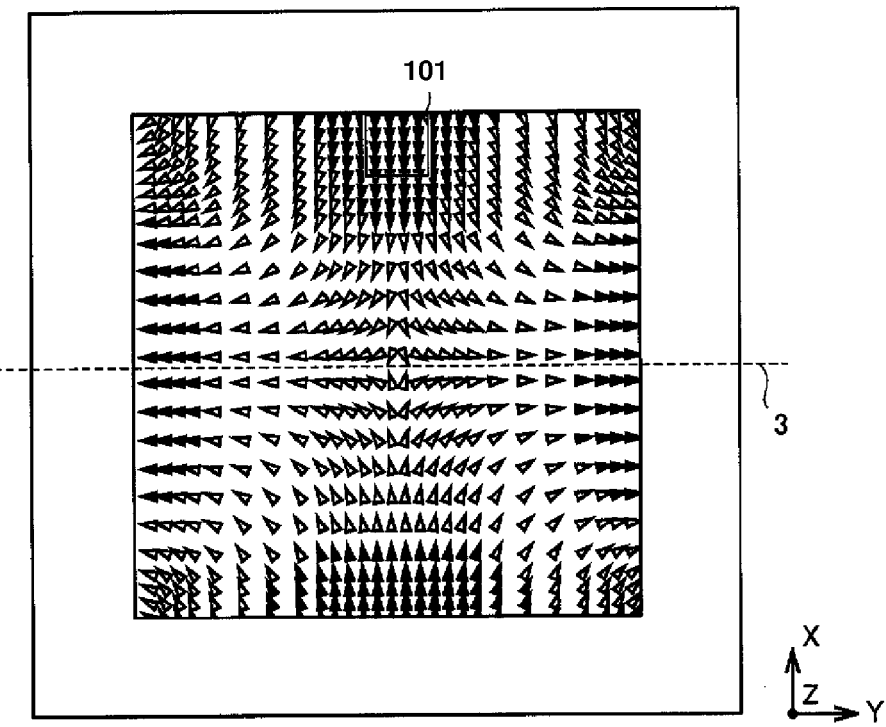
FIG. 5($a$) depicts a diagram of resonance electric field vectors in the void of the periodic structure 1 of the present invention, illustrated in FIG. 1($a$), at a frequency of 980 GHz.
Figure 5B:
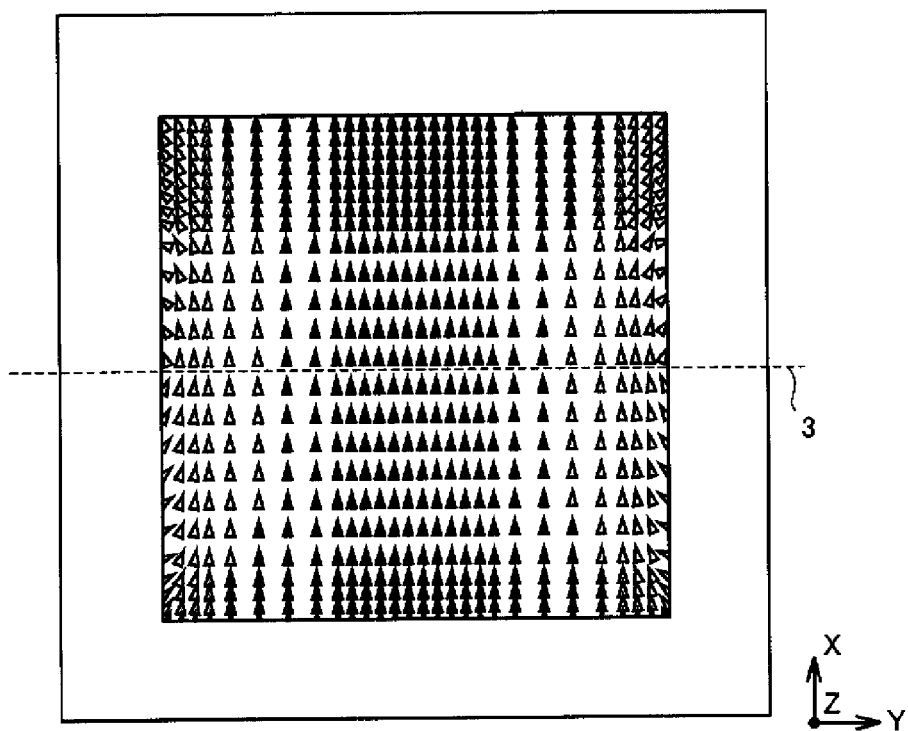

FIG. 5(a) depicts a diagram of resonance electric field vectors in the void when the periodic structure 1 of the present invention, illustrated in FIG. 1(a), is irradiated with an electromagnetic wave at a frequency of 980 GHz. FIG. 5(b) depicts a diagram of resonance electric field vectors in the void when the related-art periodic structure 9, illustrated in FIG. 1(b), is irradiated with the electromagnetic wave at a frequency of 980 GHz.

In FIGS. 5(a) and 5(b), the direction of a sharp end of a triangle (i.e., a triangle apex having a minimum angle) denotes the direction of an electric field vector. Further, a black triangle represents a portion where the electric field vector has a relatively large magnitude (i.e., the electric field intensity is relatively strong), and a white triangle represents a portion where the electric field vector has a relatively small magnitude. As seen from comparing those diagrams of electric field vectors with each other, on condition that individual voids penetrating through the periodic structure are each regarded as one waveguide, resonance having a resonance mode similar to a TE10 mode (i.e., TE10 mode-like resonance) is generated in a void 91 of the related-art periodic structure 9, illustrated in FIG. 1(b), and resonance having a resonance mode similar to a TE11 mode (i.e., TE11 mode-like resonance) is generated in the void 11 of the periodic structure 1 of the present invention, illustrated in FIG. 1(a).

The projection or the cutout, for example, is preferably provided at a position where the magnitude of the electric field vector is relatively increased in the diagram of electric field vectors, illustrated in FIG. 5(a), when the TE11 mode-like resonance is generated. The reason is that, by providing the projection or the cutout at such a position, it is possible to obtain a sharp dip waveform in the frequency characteristic of the forward-scattered electromagnetic wave or a sharp peak waveform in the frequency characteristic of the backward-scattered electromagnetic wave.

From the above-described simulation results, the following is discussed as the reason why the dip waveform is not obtained with the related-art periodic structure 9, but it is obtained only with the periodic structure 1 of the present invention, when the electromagnetic wave is perpendicularly incident on the principal surface of the flat-plate periodic structure.

The TE11 mode-like resonance generated in the void and causing the dip waveform is a resonance mode in which spatial symmetry is very high, as illustrated in FIG. 5(a). In a structure having voids arrayed in mirror symmetry with respect to an imaginary plane 3 that is perpendicular to the polarizing direction of the electromagnetic wave (i.e., in the X-direction denoted in the drawing), as in the related-art periodic structure 9, a resultant vector in one region of the void divided by the imaginary plane 3 and a resultant vector in the other region of the void are always provided by vectors having the same magnitude and the opposed directions. Therefore, a resultant vector in the entire void is always zero. Stated another way, in the related-art structure (related-art periodic structure 9), a dipole moment based on the TE11 mode-like resonance is always zero and coupling of the dipole moment with the incident electromagnetic wave is not generated, whereby the TE11 mode-like resonance is not excited. The term "dipole moment" implies a vector that is featured by the product of a directional vector extending from a negative charge to a positive charge of an electric or magnetic charge and the magnitude thereof in a three-dimensional spatial region.

In contrast, the void of the periodic structure according to the present invention does not have mirror symmetry with respect to the imaginary plane 3 that is perpendicular to the polarizing direction of the electromagnetic wave. Therefore, the resultant vector in one void region and the resultant vector in the other void region are not the same, and hence a dipole moment having a finite magnitude, instead of being zero, is generated. As a result, the dipole moment is coupled with the incident electromagnetic wave, whereby the TE11 mode-like resonance is excited.

In the above description, the measuring method is disclosed which measures the characteristics of the specimen on the basis of the phenomenon that, for example, the position of the dip waveform appearing in the frequency characteristic of the electromagnetic wave scattered forward by the flat-plate periodic structure or the peak waveform appearing in the frequency characteristic of the electromagnetic wave scattered backward by the flat-plate periodic structure is shifted with the presence of the specimen. However, the flat-plate periodic structure according to the present invention can also be used in other applications, e.g., a filter for electromagnetic waves propagating in a space (i.e., an electromagnetic filter). For example, various flat-plate periodic structures disclosed, by way of example, in this Description can be used as electromagnetic filters.

While a related-art electromagnetic filter has just a band pass characteristic allowing passage of electromagnetic waves in a certain range therethrough, the flat-plate periodic structure according to the present invention can be used as a (polar) band pass filter that additionally has an attenuation characteristic generating an attenuation pole in a frequency band, which corresponds to the dip waveform appearing in the characteristic of the forward-scattered electromagnetic wave. The reason is that, when the flat-plate periodic structure according to the present invention is used as an electromagnetic filter, the dip waveform in the frequency characteristic of the forward-scattered electromagnetic wave or the peak waveform in the frequency characteristic of the backward-scattered electromagnetic wave can be obtained in the state where the periodic structure is arranged with its principal surface being perpendicular to the propagating direction of the electromagnetic wave.

The flat-plate periodic structure according to the present invention, which is usable as the electromagnetic filter, can be used in a mobile communication device, a broadcasting device, etc.

EXAMPLES

The present invention will be described in more detail below in connection with EXAMPLES, but the present invention is not restricted to the following EXAMPLES.

Example 1

EXAMPLE 1 represents the case where, in the flat-plate periodic structure, the projection or the cutout is added to a portion of a surface defining the void.

[Simulated Calculations on Periodic Structures Illustrated in FIGS. 6(a) to 11(a)]

Figure 6A:
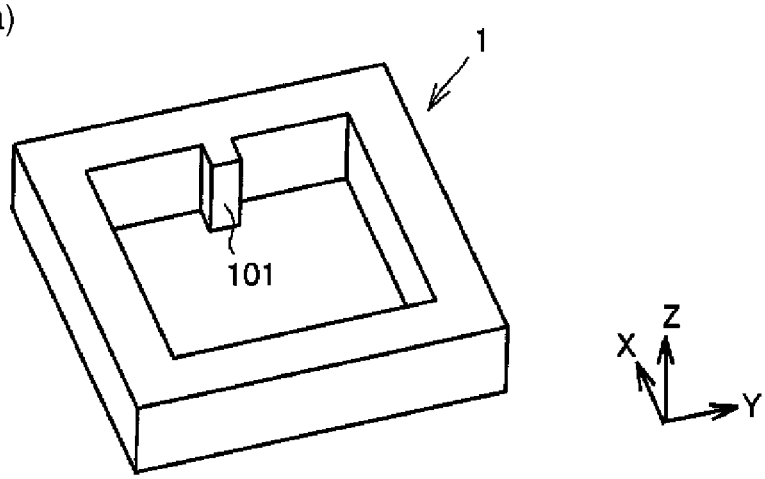
FIG. 6($a$) is a perspective view illustrating a void in another example of the flat-plate periodic structure according to the present invention.
Figure 6B:
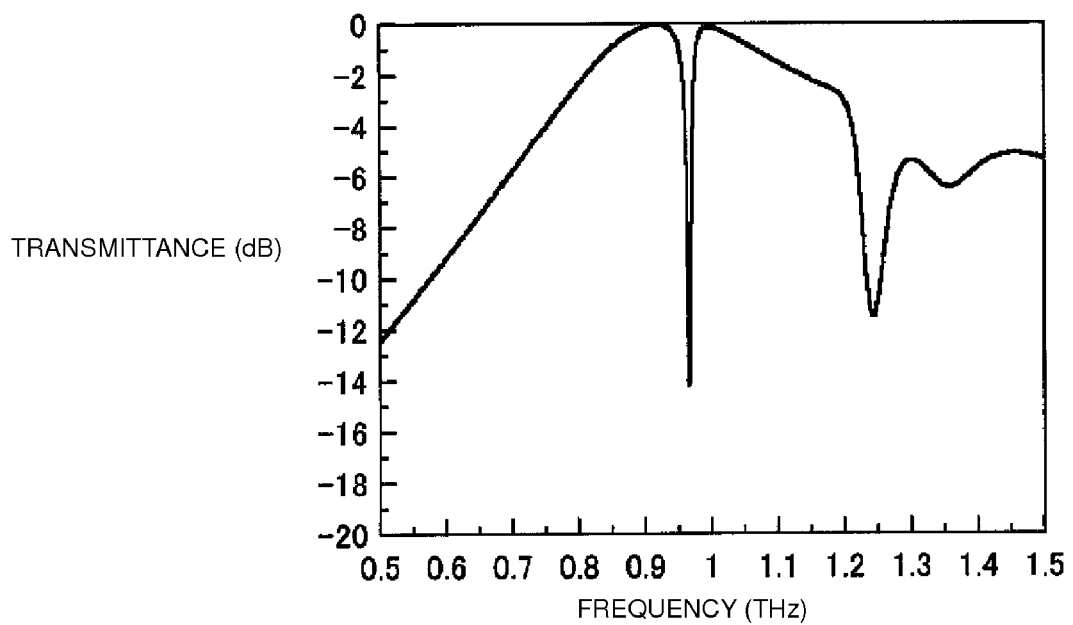
Figure 7A:
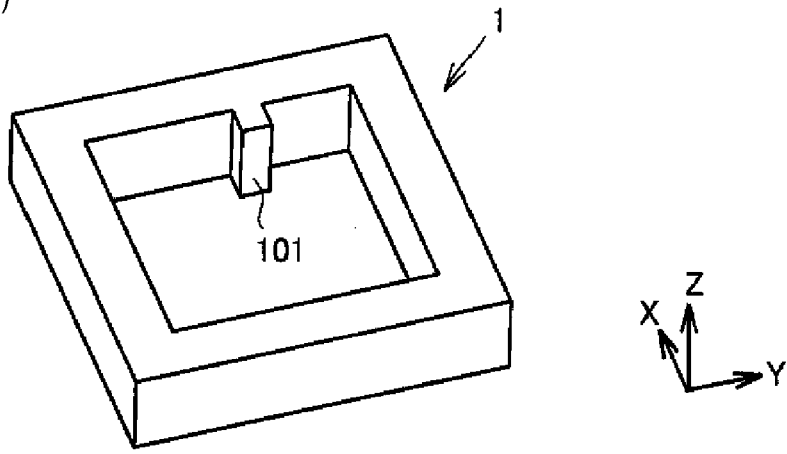
FIG. 7($a$) is a perspective view illustrating a void in still another example of the flat-plate periodic structure according to the present invention.
Figure 7B:
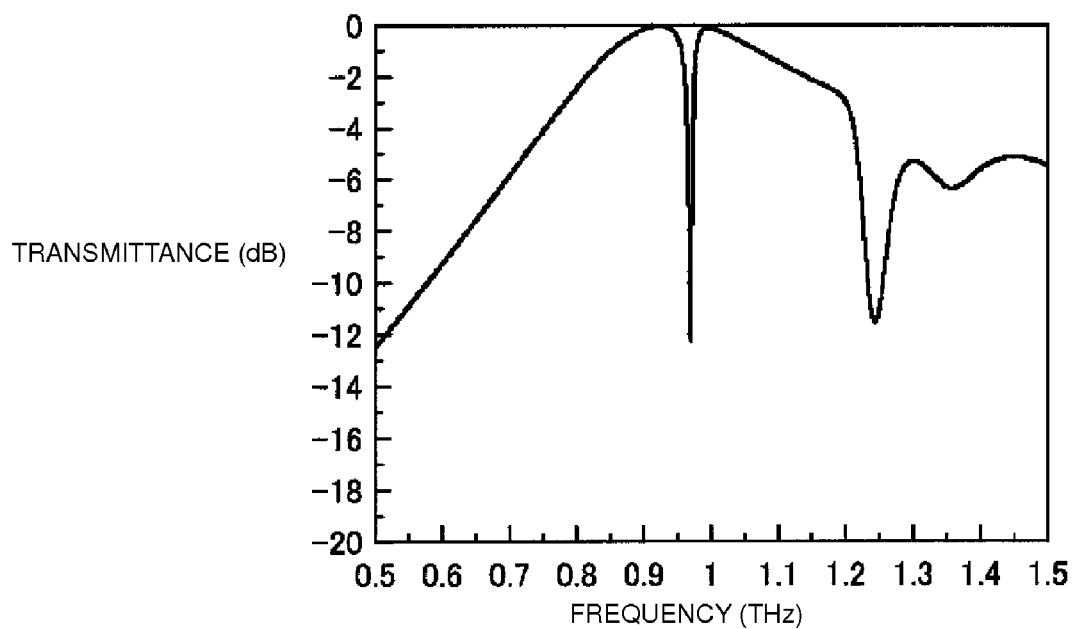
Figure 8A:
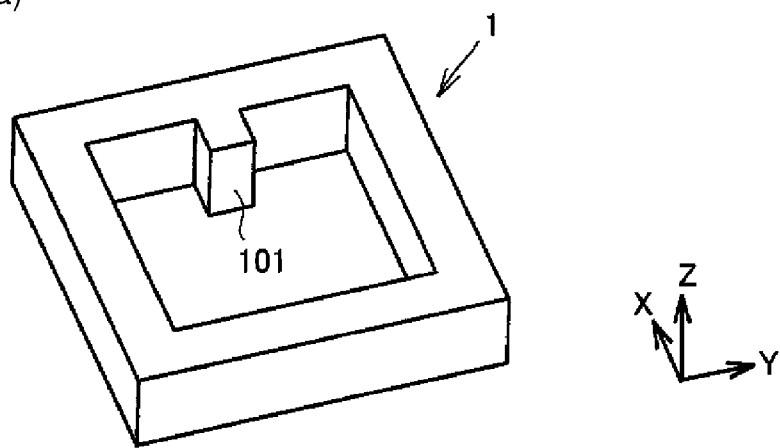
FIG. 8($a$) is a perspective view illustrating a void in still another example of the flat-plate periodic structure according to the present invention.
Figure 8B:
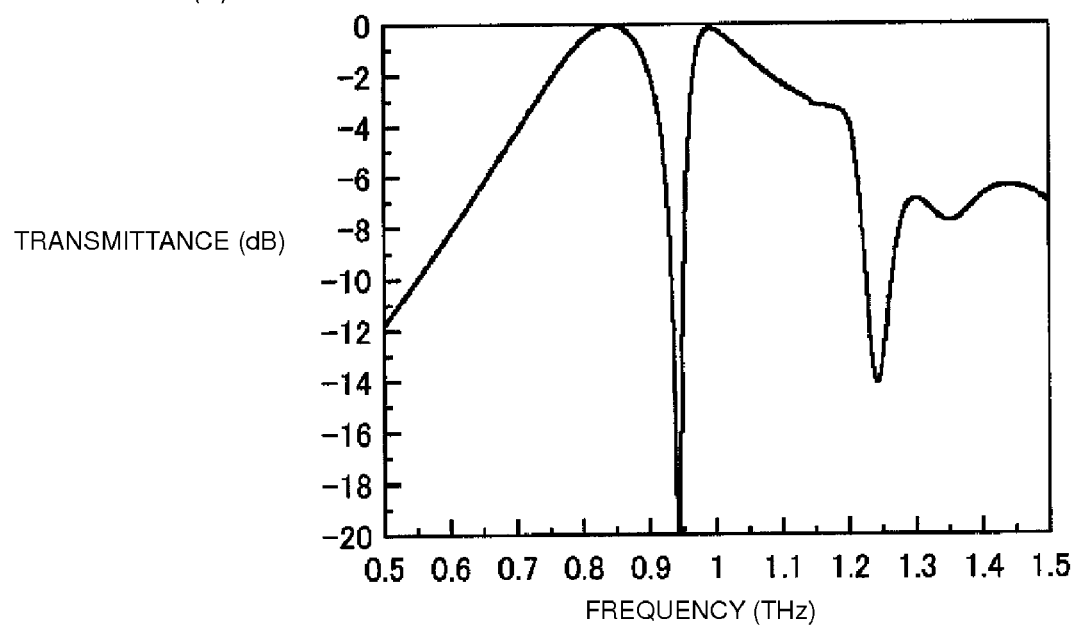
Figure 9A:
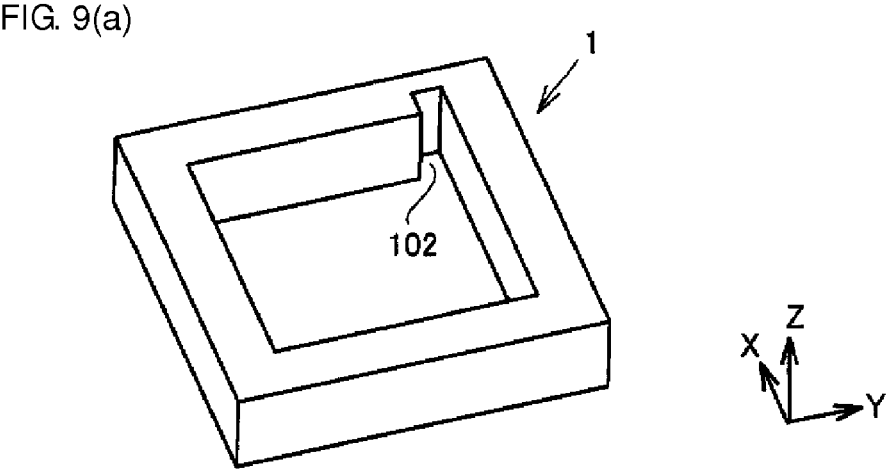
FIG. 9($a$) is a perspective view illustrating a void in still another example of the flat-plate periodic structure according to the present invention.
Figure 9B:
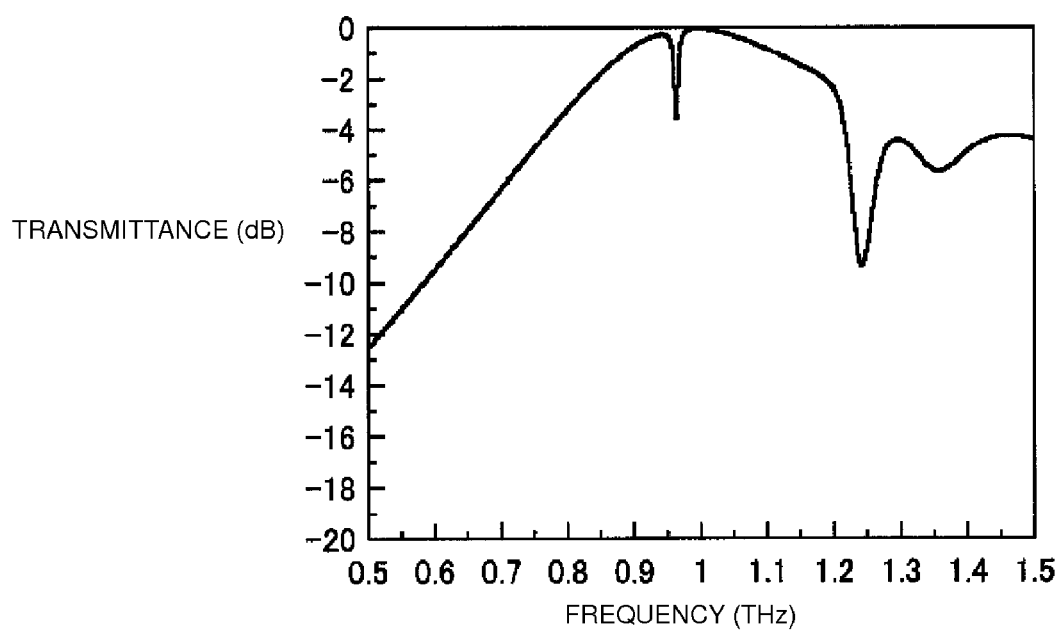
Figure 10A:
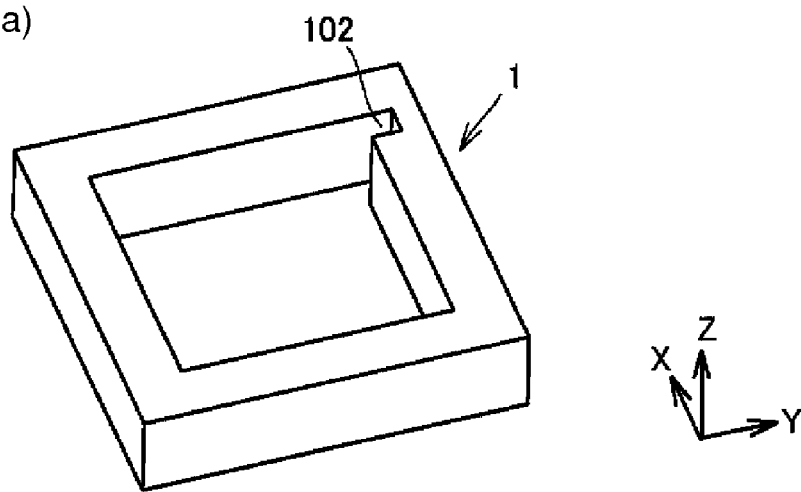
FIG. 10($a$) is a perspective view illustrating a void in still another example of the flat-plate periodic structure according to the present invention.
Figure 10B:
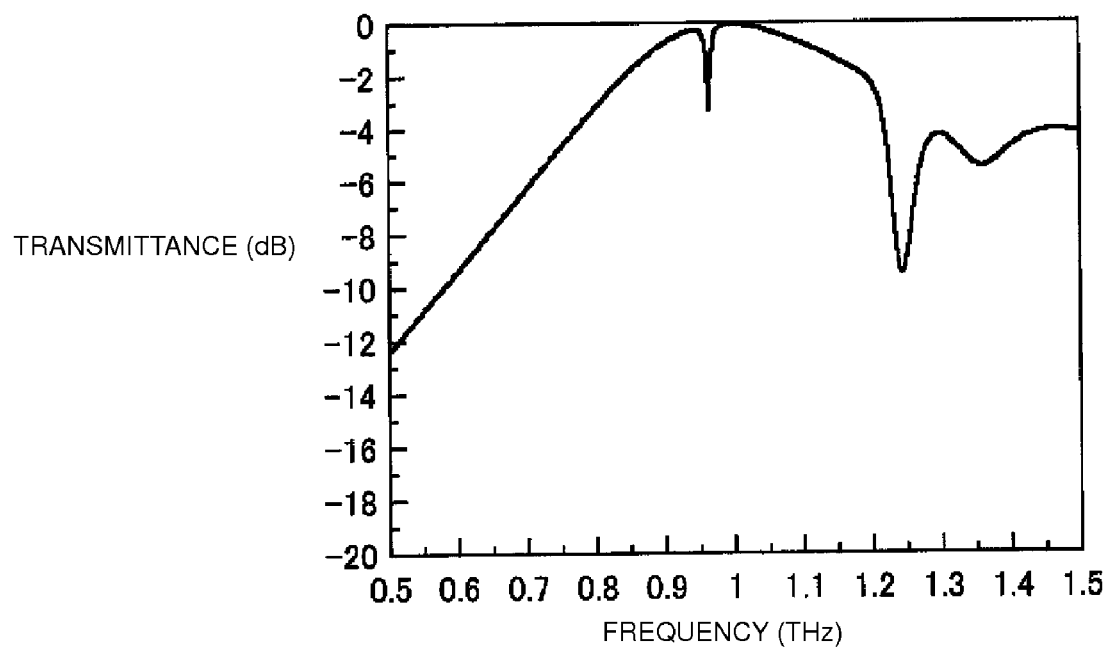
Figure 11A:
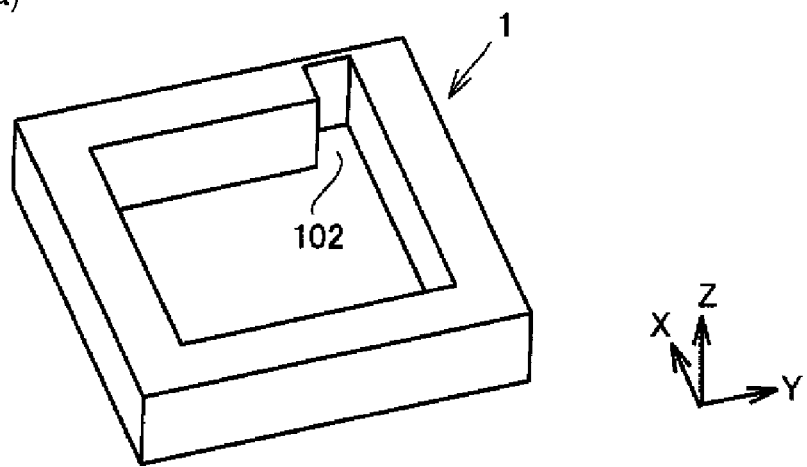
FIG. 11($a$) is a perspective view illustrating a void in still another example of the flat-plate periodic structure according to the present invention.
Figure 11B:
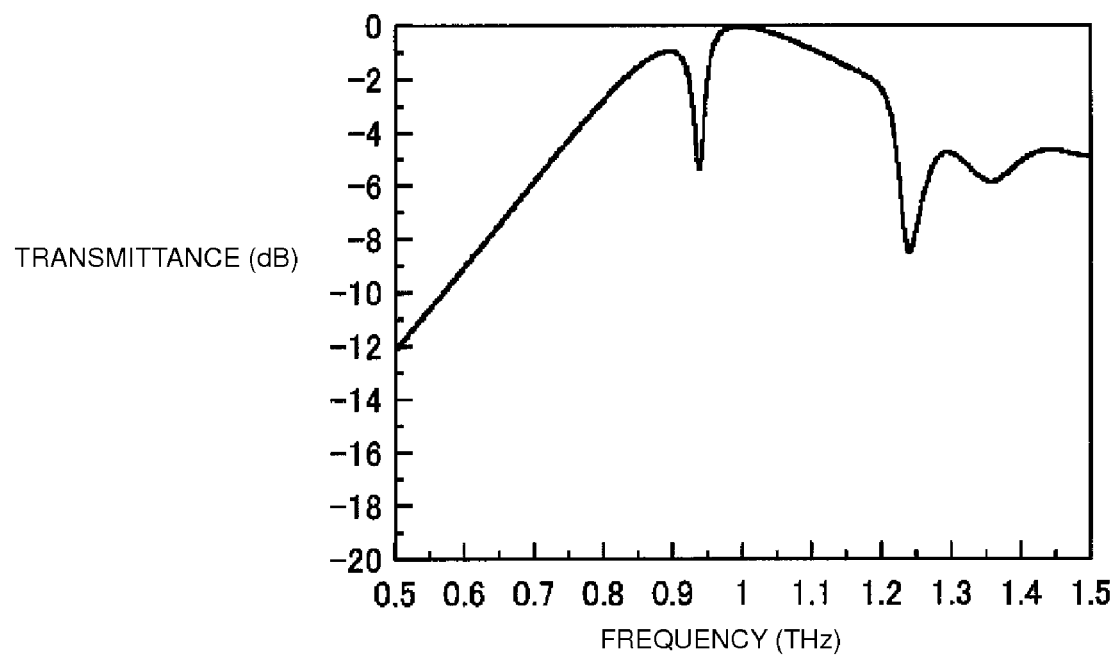

FIGS. 6(a) to 11(a) illustrate six types of void configurations in flat-plate periodic structures according to the present invention. FIG. 6(a) illustrates a periodic structure 1 in which the projection 101 is formed near a center of one of side surfaces defining the void. FIG. 7(a) illustrates a periodic structure 1 in which the position of the projection 101, illustrated in FIG. 6(a), is moved from the vicinity of the center of one of the void side surfaces. FIG. 8(a) illustrates a periodic structure 1 in which the size of the projection 101, illustrated in FIG. 6(a), is increased. FIG. 9(a) illustrates a periodic structure 1 in which a cutout 102 is formed near an end of one of void side surfaces. FIG. 10(a) illustrates a periodic structure 1 in which the position of the cutout 102, illustrated in FIG. 9(a), is changed. FIG. 11(a) illustrates a periodic structure in which the size of the cutout, illustrated in FIG. 9(a), is changed. It is to be noted that each of those drawings illustrates only a unit structure including one void of the periodic structure 1, and a periodic structure obtained by infinitely two-dimensionally arraying the unit structure in succession is set as a simulation target. The propagating direction of the electromagnetic wave is a direction perpendicular to the principal surface of the periodic structure 1 (i.e., in the Z-direction denoted in (a) in each of FIGS. 6 to 11), and the principal surface of the periodic structure 1 is irradiated with the electromagnetic wave such that the polarizing direction of the electromagnetic wave is aligned with the X-direction denoted in (a) in each of FIGS. 6 to 11 (those assumptions are similarly applied to the whole of the following description).

Figure 22A:
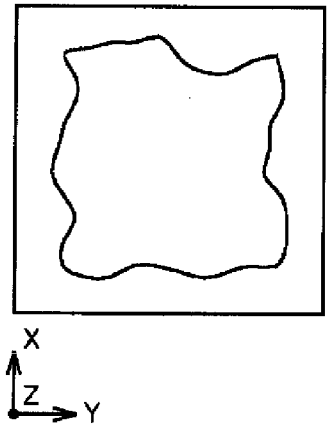
FIG. 22(a) is a front view illustrating a void in an example of the flat-plate periodic structure according to the present invention in which the contour of the void has a random shape.

FIGS. 6(b) to 11(b) depict frequency characteristics of transmittance [dB], which were calculated respectively with electromagnetic field simulations on the periodic structures, illustrated in FIGS. 6(a) to 11(a), on the same conditions as those described above with reference to FIGS. 2(a) and 2(b). Commercially-available simulated calculation software (MICROSTRIPES 2009 made by CST AG.) was used for the simulated calculations. That simulation software can execute simulation based on the figure of a unit structure of a periodic structure that is virtually fabricated on the software. Accordingly, even for a periodic structure having a void in a random shape such as illustrated in FIG. 22(a) (described later), the simulated calculation can be executed by forming a drawing of a unit structure, illustrated in FIG. 22(a), on the software. It is to be noted that, while the periodic structures illustrated in FIGS. 6(a) to 11(a) are depicted substantially in the same scale as that of the figure formed on the simulation software, detailed information of the figure (e.g., the size of each void, etc.) is omitted here because, from the viewpoint of explaining the advantageous effects of the present invention, the point regarding symmetry in shape of the void (i.e., the void shape being not mirror symmetric with respect to the imaginary plane perpendicular to the polarizing direction of the applied electromagnetic wave) is important and the detailed figure information is not essentially important.

As seen from the simulation results described above, even when the electromagnetic wave is applied to the principal surface of the flat-plate periodic structure 1 from the direction perpendicular to the principal surface, the dip waveform attributable to the TE11 mode-like resonance is generated by using the periodic structure in which the projection or the cutout is added to a portion of the void such that the void shape is made not mirror symmetric with respect to the imaginary plane perpendicular to the polarizing direction of the electromagnetic wave.

Figure 28:
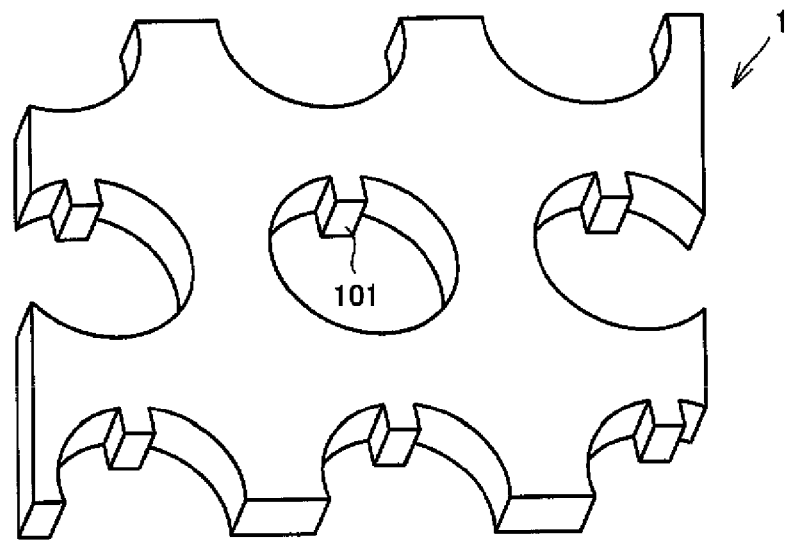
FIG. 28 is a perspective view illustrating a void in still another example of the flat-plate periodic structure according to the present invention.
Figure 29:
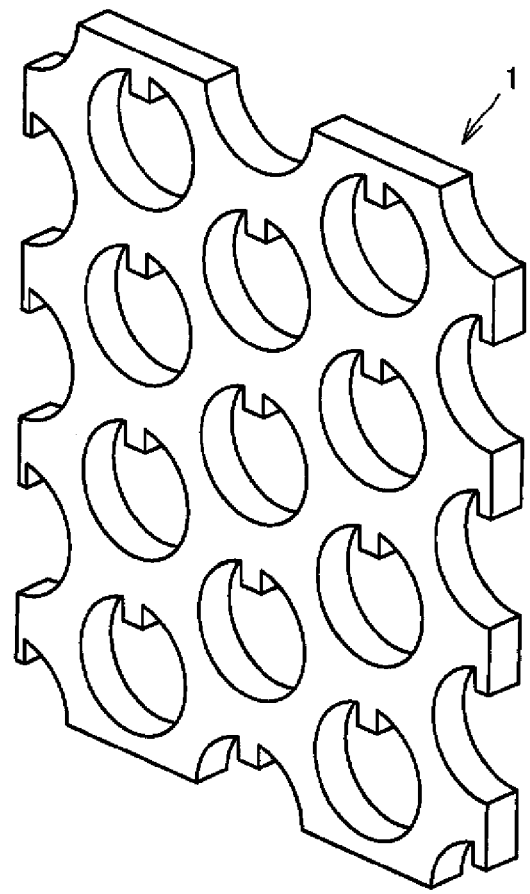
FIG. 29 is a perspective view illustrating a void in still another example of the flat-plate periodic structure according to the present invention.

While the square shape is employed in EXAMPLE 1 as the shape of the void penetrating through the flat-plate periodic structure, similar advantageous effects to those described above can also be obtained even in the periodic structure 1 having circular voids as illustrated in FIG. 28, for example, by providing the projection 101 for each circular void in a similar way. Further, while EXAMPLE 1 employs the flat-plate structure in which the voids penetrating through the flat-plate periodic structure are periodically arrayed in a square lattice pattern in the planar direction of the principal surface of the flat-plate periodic structure, similar advantageous effects can be obtained even in a periodic structure having voids arrayed in a triangular lattice pattern as illustrated in FIG. 29, for example, insofar as the voids have the shape satisfying the above-described conditions.

[Actual Measurement on Periodic Structure Illustrated in FIG. 6(a)]

The flat-plate periodic structure, illustrated in FIG. 6(a), was actually fabricated and a frequency characteristic obtained by applying the electromagnetic wave to the flat-plate periodic structure was evaluated. Procedures of fabricating the periodic structure are as follows.

A conductive plate (made of Cu) having a smooth surface of 300 mm square was prepared, and a photosensitive resin layer was coated and dried in a thickness of 100 μm on one of the opposite sides of the conductive plate. A photomask having the periodic structure, illustrated in FIG. 6(a), formed in the principal surface thereof was prepared, and portions of the photosensitive resin layer corresponding to the voids, illustrated in FIG. 6(a), was UV-cured by using the photomask. An uncured resin portion corresponding to a structure portion, illustrated in FIG. 6(a), was removed by rinsing, whereby the conductive plate was made exposed. A polymer solution was coated and dried on the surface that had been subjected to patterning with photolithography, whereby a very thin polymer layer, capable of being peeled off, was formed on the exposed portion of the conductive plate.

By placing the conductive plate, obtained as described above, in a Ni electric-field plating bath and supplying a current, a Ni plated film was formed in a thickness of 60 μm only in the portion where the polymer layer was not formed and the conductive plate was exposed. After the plating, the cured resin remaining on the conductive plate was removed with a solvent, and a Ni plated structure was peeled off from the conductive plate. Thus, a Ni-made flat-plate periodic structure having the thickness of 60 μm was obtained in which the voids, each illustrated in FIG. 6(a), were periodically arrayed on a principal surface of the structure in the vertical and horizontal directions thereof.

Electroless Au plating was performed on the Ni-made flat-plate periodic structure obtained as described above, whereby a periodic structure coated with Au was obtained.

By using the flat-plate periodic structure fabricated as described above, a frequency characteristic of an electromagnetic wave scattered forward (i.e., a frequency characteristic of an electromagnetic wave having transmitted through the periodic structure), when the electromagnetic wave was applied to the principal surface of the periodic structure from the direction perpendicular to the principal surface, was actually measured by using the apparatus configuration, illustrated in FIG. 12, under the same conditions as the above-described simulation conditions. While, in this measurement, parallel light was used as the electromagnetic wave applied to the flat-plate periodic structure in FIG. 12, an optical system including any of parallel light and condensed light may be used in the present invention.

In the measuring method according to the present invention, as illustrated in FIG. 12, the electromagnetic wave is applied to the principal surface of the flat-plate periodic structure 1 from the direction perpendicular to the principal surface. Stated another way, given that an angle formed between a linear line perpendicular to the principal surface of the flat-plate periodic structure 1 and the propagating direction of the electromagnetic wave is an incidence angle α, the incidence angle α is 0° in the measuring method according to the present invention. In the related-art measuring method, the incidence angle α of the electromagnetic wave is set to several degrees instead of being 0°. In the present invention, by making the electromagnetic wave perpendicularly incident on the principal surface of the flat-plate periodic structure, a mechanical component for rotating the periodic structure, which is needed in the case of oblique incidence, is no longer needed, and the influence due to an error (generally ±0.5°) in rotational angle of the mechanical component is suppressed. Therefore, a variation in the measurement caused by a variation in the incidence angle of the electromagnetic wave is reduced and sensitivity in measuring the specimen is increased.

Figure 15:
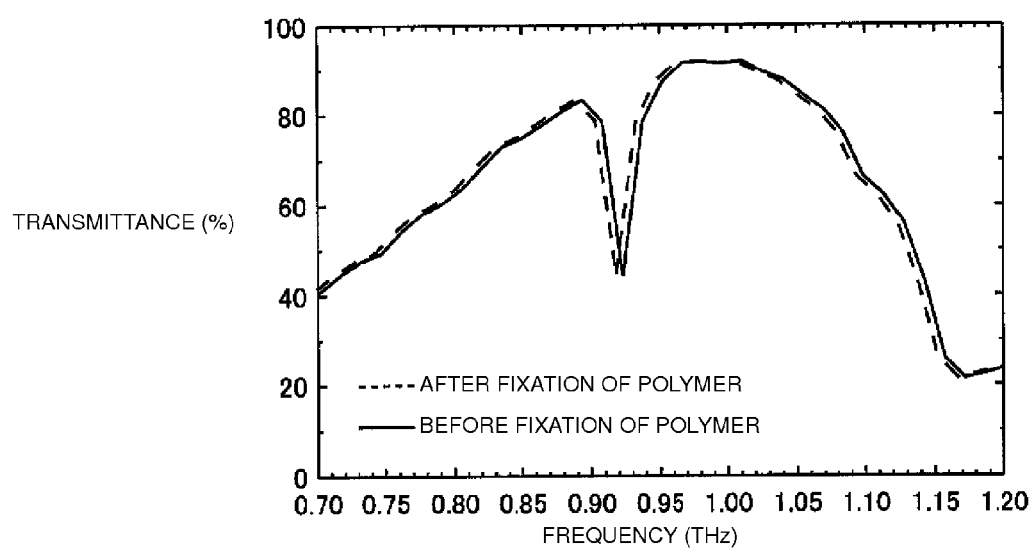
FIG. 15 depicts frequency characteristics of transmittance (%) with the flat-plate periodic structure of the present invention, illustrated in FIG. 6($a$), before and after fixation of a polymer.

FIG. 15 (solid line in FIG. 15) depicts the frequency characteristic actually measured, as described above, on the periodic structure illustrated in FIG. 6(a). From the result of FIG. 15, it is understood, as with the result of the simulated calculation depicted in FIG. 6(b), that the dip waveform attributable to the TE11 mode-like resonance is generated by applying the electromagnetic wave to the flat-plate periodic structure 1, illustrated in FIG. 6(a), from the direction perpendicular to the principal surface of the flat-plate periodic structure.

[Actual Measurement on Related-Art Periodic Structure]

Figure 14:
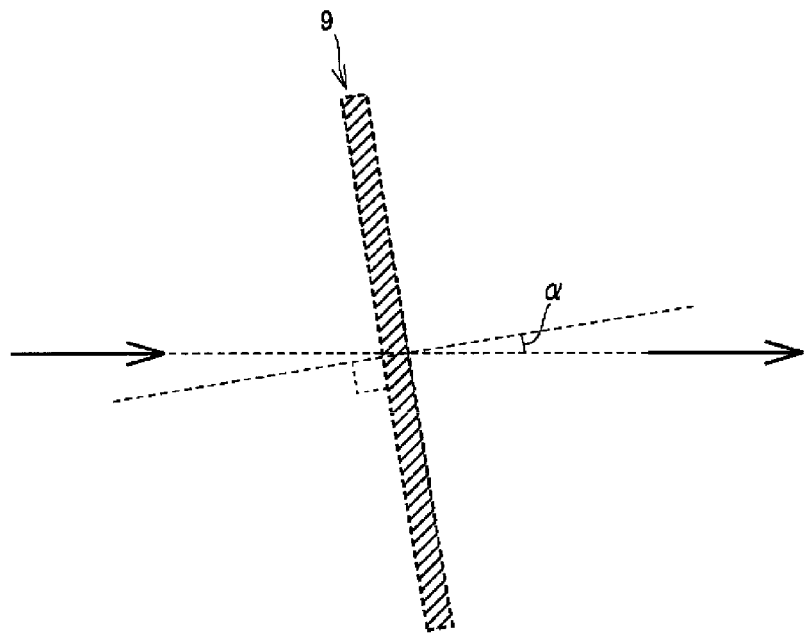
FIG. 14 is a schematic sectional view to explain an arrangement of the flat-plate periodic structure of the related art.
Figure 16:
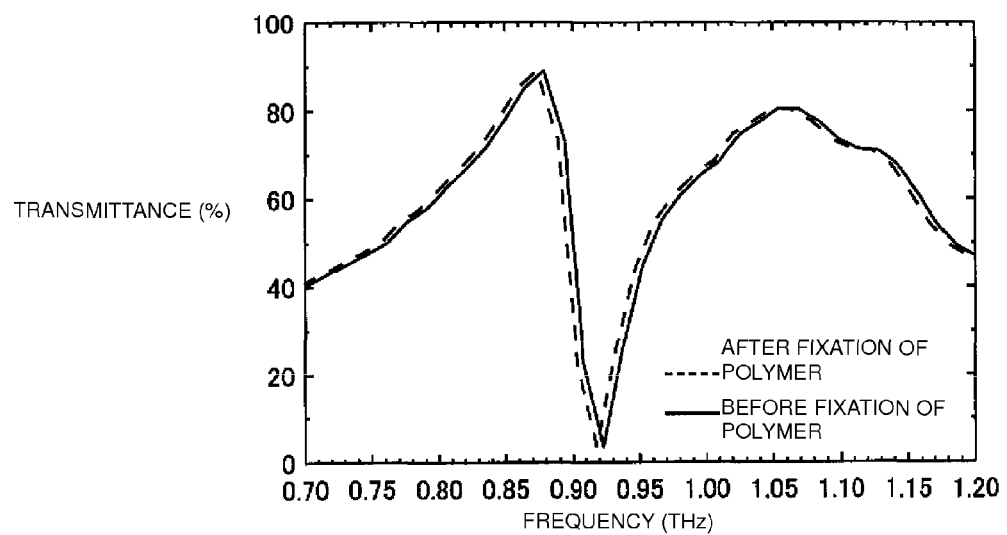
FIG. 16 depicts frequency characteristics of transmittance (%) with the flat-plate periodic structure of the related art before and after fixation of a polymer.

As a comparative reference, the flat-plate periodic structure of the related art (i.e., the periodic structure 9 illustrated in FIG. 1(b)), having a construction obtained by removing the projection 101 from the structure illustrated in FIG. 6(a), was fabricated in a similar manner to the above-described fabrication method. Further, a frequency characteristic of transmittance with the periodic structure 9 was actually measured by setting the periodic structure in the apparatus configuration, illustrated in FIG. 12, in an inclined state such that an angle α formed between the direction perpendicular to the principal surface of the periodic structure 9 and the propagating direction of the electromagnetic wave was 9° as illustrated in FIG. 14. FIG. 16 (solid line in FIG. 16) depicts the obtained frequency characteristic of transmittance.

As seen from comparing the frequency characteristics depicted by the solid line in FIG. 15 and by the solid line in FIG. 16, the dip waveform appearing in FIG. 15 with the method according to the present invention has a band width narrower and sharper than that appearing in FIG. 16 with the related-art method.

[Actual Measurement on Periodic Structure Before and After Fixation of Polymer]

The following comparison was performed to confirm the advantageous effects. As a specimen, 10 mL of an aqueous solution of a polymer (molecular weight of 6000) having thiol group terminals was prepared with a concentration of 10 μg/mL. The periodic structure of the present invention, illustrated in FIG. 6(a), which was fabricated in the above-described [Actual Measurement on Periodic Structure Illustrated in FIG. 6(a)], and the related-art periodic structure illustrated in FIG. 1(b), which was fabricated in the above-described [Actual Measurement on Related-Art Periodic Structure], were each separately put in the prepared aqueous solution and left to stand for about 4 hours. Thus, two types of samples were prepared in each of which the polymer having thiol group terminals (i.e., the specimen) was fixated to Au of the periodic structure.

Each sample was actually measured on the frequency characteristic of transmittance after the fixation of the polymer in the same manner as that described above in [Actual Measurement on Periodic Structure Illustrated in FIG. 6(a)]. A broken line in FIG. 15 represents the measurement result on the periodic structure of the present invention after the fixation of the polymer. Also, a broken line in FIG. 16 represents the measurement result on the related-art periodic structure after the fixation of the polymer.

From FIGS. 15 and 16, changes in the transmittance between before and after the fixation of the polymer at a frequency of 923 GHz were determined. When the periodic structure of the present invention was used (FIG. 15), the transmittance before the fixation of the polymer was 44.2% and the transmittance after the fixation of the polymer was 56.4%. Thus, the change rate of transmittance between before and after the fixation of the polymer was 12.2%. On the other hand, when the related-art periodic structure was used (FIG. 16), the change rate of the transmittance was comparatively small. More specifically, the transmittance before the fixation of the polymer was 3.4% and the transmittance after the fixation of the polymer was 11.4%. Thus, the change rate of transmittance between before and after the fixation of the polymer was 7.0%.

As seen from the above results, the measuring method according to the present invention can provide a sharper dip waveform having a narrower band width than that with the related-art measuring method, and can increase the extent of characteristic change caused by the presence of the polymer having thiol group terminals, i.e., the specimen, which is attached to the flat-plate periodic structure. Hence, an increase of measurement sensitivity can be achieved with the present invention.

While EXAMPLE 1 has been described in connection with the case where the specimen is directly attached to the structure by utilizing the Au-thiol coupling, the measurement may also be performed in an indirectly attached state, such as obtained by pressing a specimen in the form of, e.g., a film against the principal surface of the structure. Further, the measurement may be performed by setting, as an initial state, a state where a probe molecule, e.g., an antibody, a sugar chain, or DNA, is fixated to the structure, and by preparing, as an attached state, a state where a specimen, e.g., an antigen, a protein, a virus, or DNA, is specifically fixated to the probe molecule (this point is similarly applied to the following EXAMPLE 4 as well).

[Comparison between Simulated Calculation and Actual Measurement on Periodic Structure Illustrated in FIG. 1(a)]

Figure 17:
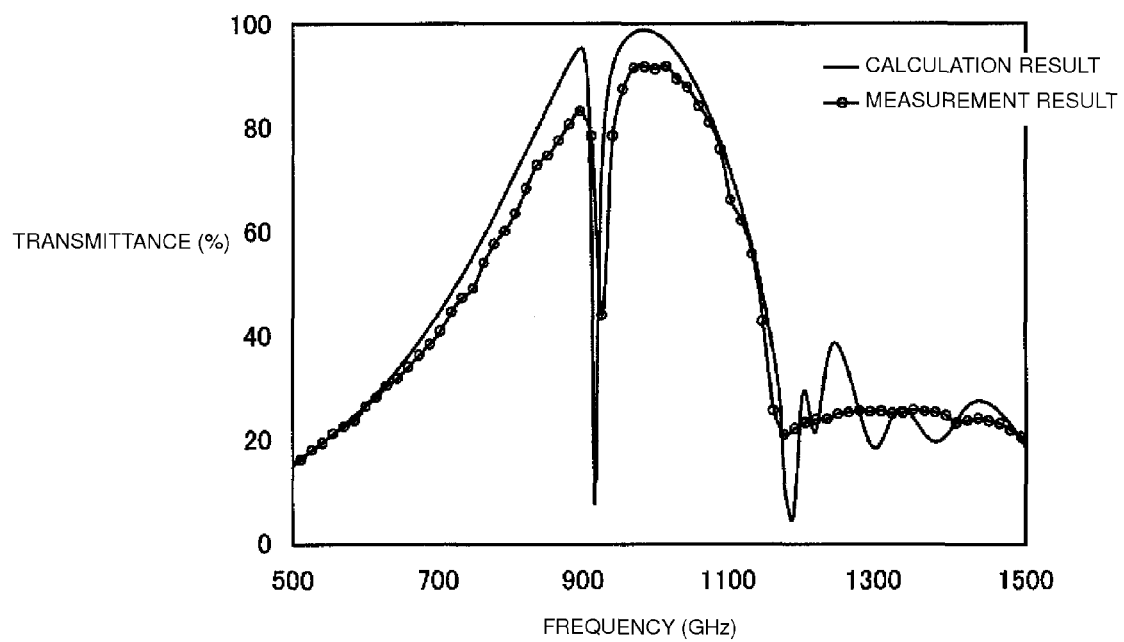
FIG. 17 depicts frequency characteristics (calculation result and measurement result) of transmittance (%) with the periodic structure 1 of the present invention, illustrated in FIG. 1($a$).

The periodic structure 1 of the present invention, illustrated in FIG. 1(a), was fabricated in the same manner as that described above in [Actual Measurement on Periodic Structure Illustrated in FIG. 6(a)], and the frequency characteristic was actually measured. Further, simulated calculation on the periodic structure 1 of the present invention, illustrated in FIG. 1(a), was executed in the same manner as that described above in [Simulated Calculations on Periodic Structures Illustrated in FIGS. 6(a) to 11(a)]. However, the unit of transmittance was set to %. FIG. 17 depicts the results of both the actual measurement and the simulated calculation.

As seen from the results depicted in FIG. 17, the shapes of the dip waveforms are substantially matched with each other between a transmittance spectrum obtained from the actually measured values and a transmittance spectrum obtained with the simulated calculation.

Example 2

EXAMPLE 2 represents the case where the void has an asymmetric shape in its entirety with respect to the imaginary plane perpendicular to the polarizing direction of the electromagnetic wave.

Figure 22B:
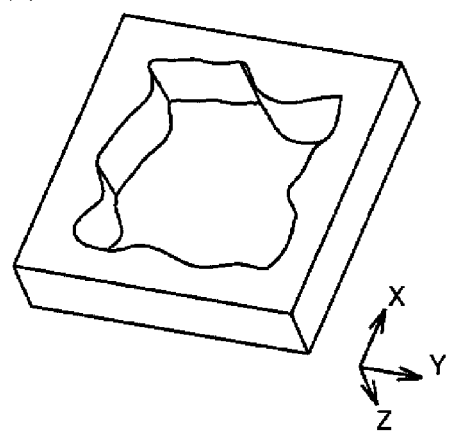
FIG. 22(b) is a perspective view illustrating the same void as that in FIG. 22(a).
Figure 22C:
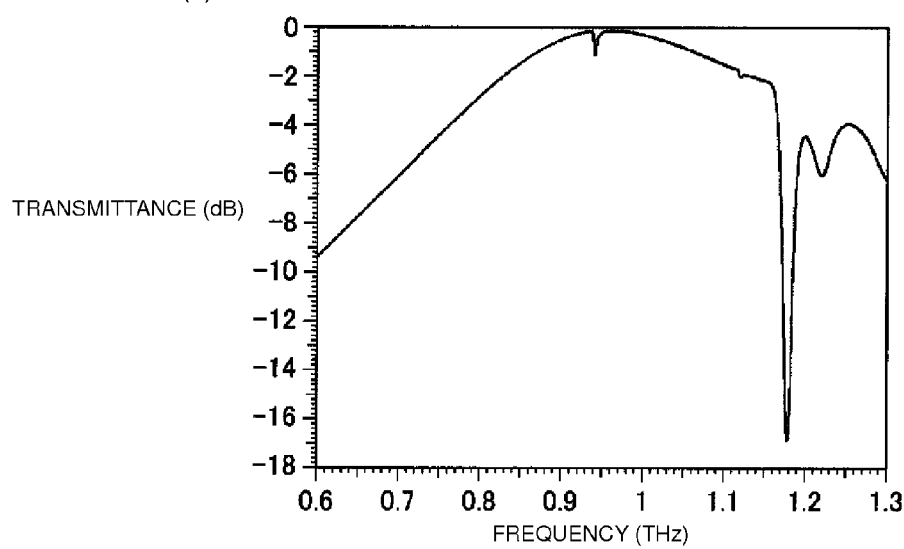
FIG. 22(c) depicts the calculation result of a frequency characteristic of transmittance [dB] with the periodic structure illustrated in FIGS. 22(a) and 22(b).
Figure 23A:
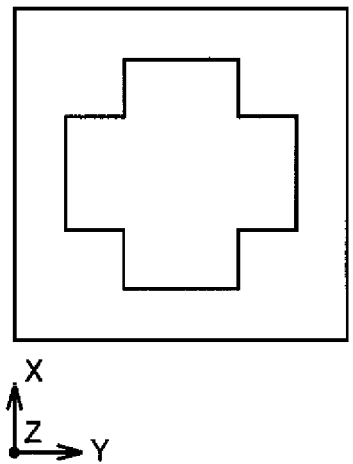
FIG. 23(a) is a front view illustrating a void in a comparative example (related art) of the flat-plate periodic structure in which the void has a crossed shape.
Figure 23B:
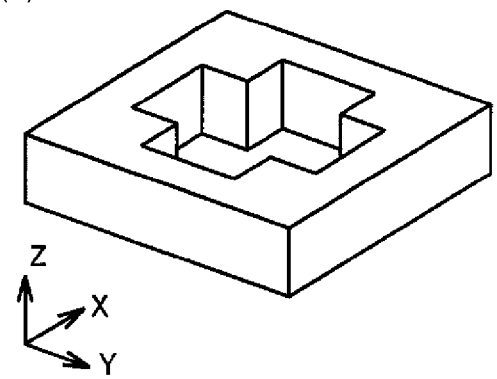
FIG. 23(b) is a perspective view illustrating the same void as that in FIG. 23(a).
Figure 23C:
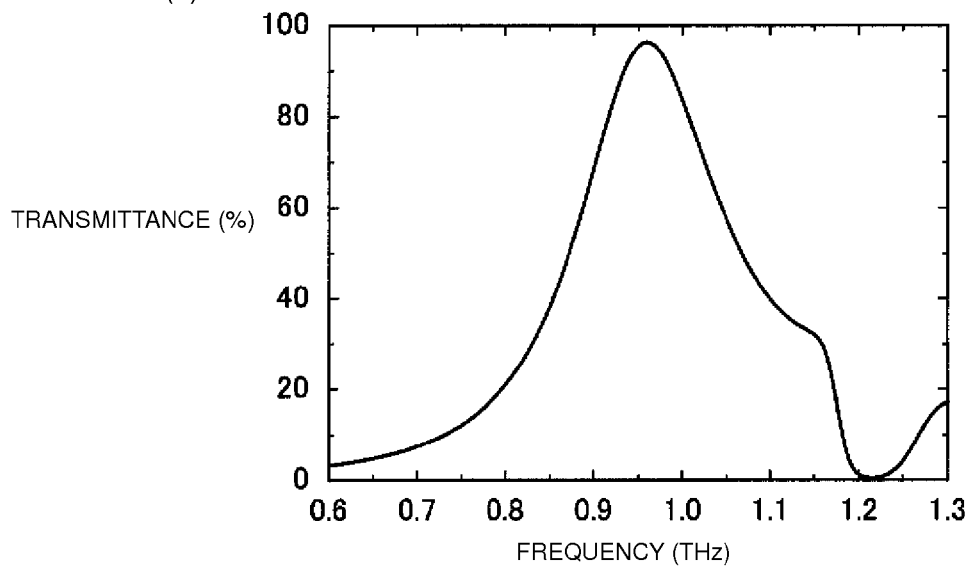
FIG. 23(c) depicts the calculation result of a frequency characteristic of transmittance [%] with the periodic structure illustrated in FIGS. 23(a) and 23(b).
Figure 24A:
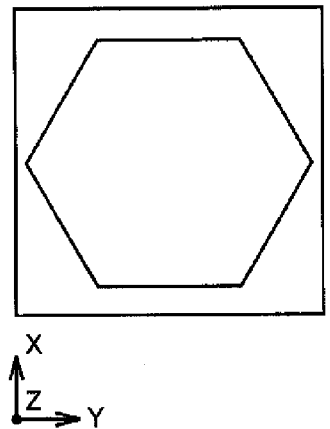
[FIG. 24(a) is a front view illustrating a void in a comparative example (related art) of the flat-plate periodic structure in which the void has a regular hexagonal shape.
Figure 24B:
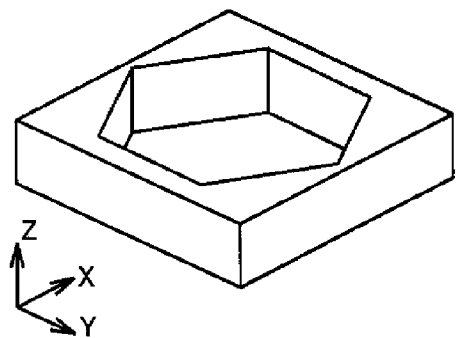
FIG. 24(b) is a perspective view illustrating the same void as that in FIG. 24(a).
Figure 24C:
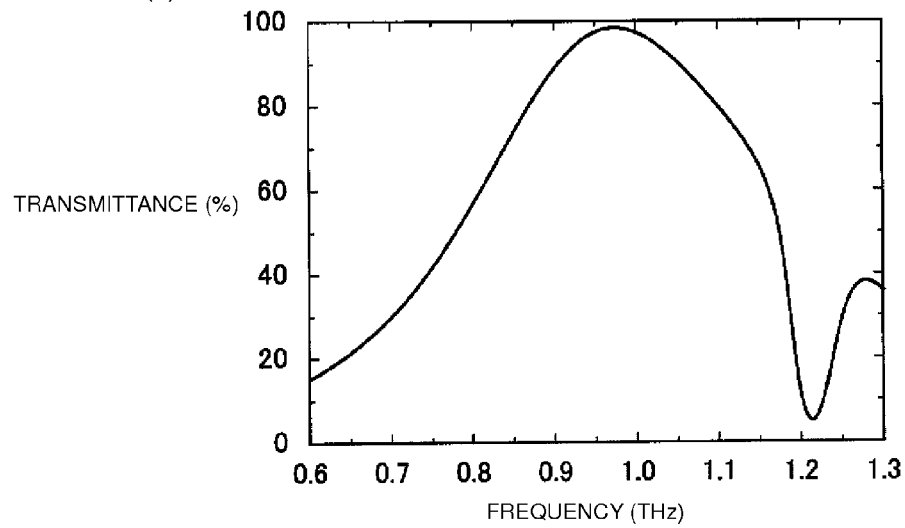
FIG. 24(c) depicts the calculation result of a frequency characteristic of transmittance [%] with the periodic structure illustrated in FIGS. 24(a) and 24(b).

In the drawings, (a) in each of FIGS. 18 to 21 and (a) and (b) in each of FIGS. 22 to 24 illustrate five types of void configurations in the flat-plate periodic structures according to the present invention and two types of void configurations in the flat-plate periodic structures as COMPARATIVE EXAMPLES. FIG. 18(a) represents the case where the void shape (as viewed in the direction perpendicular to the principal surface of the periodic structure) is trapezoidal. FIG. 19(a) represents the case where the void has a convex shape (i.e., a shape obtained by centrally projecting one side of a rectangle). FIG. 20(a) represents the case where the void has a regular pentagonal shape. FIG. 21(a) represents the case where the void has a star-like shape. FIGS. 22(a) and 22(b) represent the case where the void has a random contour shape as illustrated. FIGS. 23(a) and 23(b) represent COMPARATIVE EXAMPLE (related art) in which the void has a crossed shape. FIGS. 24(a) and 24(b) represent COMPARATIVE EXAMPLE (related art) in which the void has a regular hexagonal shape.

In the drawings, (b) in each of FIGS. 18 to 21 and (c) in each of FIGS. 22 to 24 depict the frequency characteristics of transmittance calculated for the individual periodic structures, illustrated in (a) in each of FIGS. 18 to 21 and in (a) and (b) in each of FIGS. 22 to 24, with the electromagnetic simulations on the same conditions as those described above with reference to FIGS. 2(a) and 2(b). As seen from those results, even when the electromagnetic wave is applied to the principal surface of the flat-plate periodic structure 1 from the direction perpendicular to the principal surface, the dip waveform attributable to the TE11 mode-like resonance is generated by using the periodic structure in which the entire shape of the void is set to be not mirror symmetric with respect to the imaginary plane perpendicular to the polarizing direction of the electromagnetic wave.

While, in EXAMPLE 2, the shape of the void penetrating through the flat-plate structure is, e.g., trapezoidal, convex, regular pentagonal, or star-like, similar advantageous effects can also be obtained even with other shapes (such as the shape illustrated in FIGS. 22(a) and 22(b)) insofar as those shapes satisfy the above-described conditions in the present invention. Further, while EXAMPLE 2 employs the structure in which the voids penetrating through the flat-plate structure are periodically arrayed in a square lattice pattern in the planar direction of the principal surface of the flat-plate structure, similar advantageous effects can be obtained even in a periodic structure having voids arrayed in a triangular lattice pattern insofar as the void has the shape satisfying the above-described conditions.

Figure 18A:
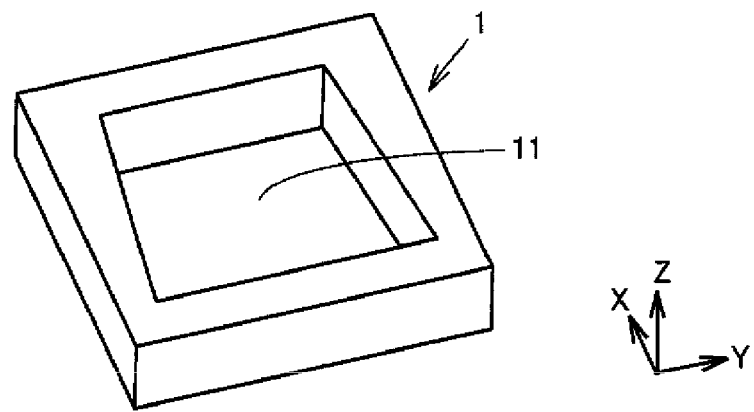
FIG. 18($a$) is a perspective view illustrating a void in an example of the flat-plate periodic structure according to the present invention in which the void has a trapezoidal shape.
Figure 18B:
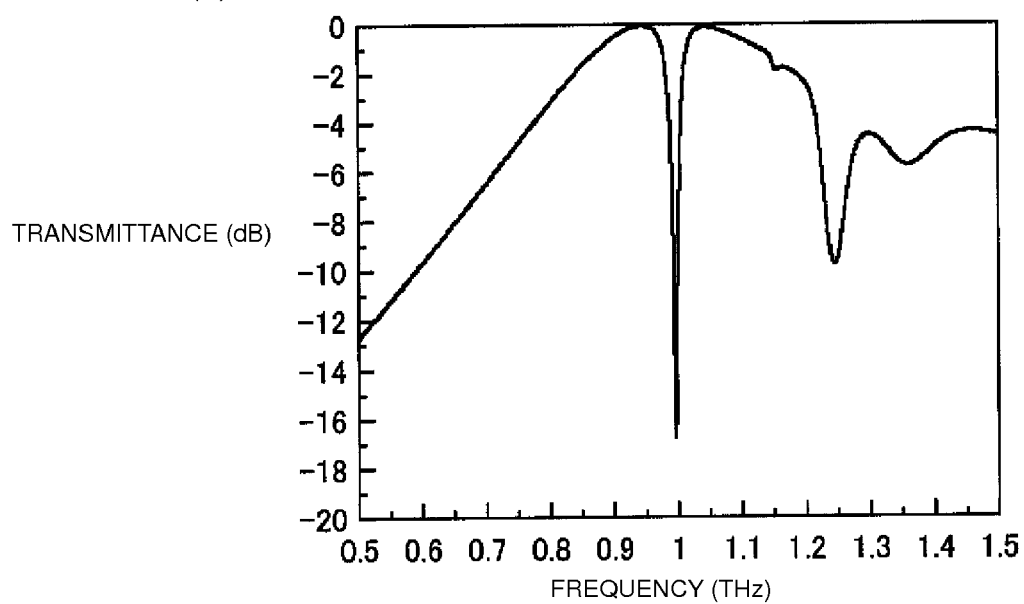
Figure 19A:
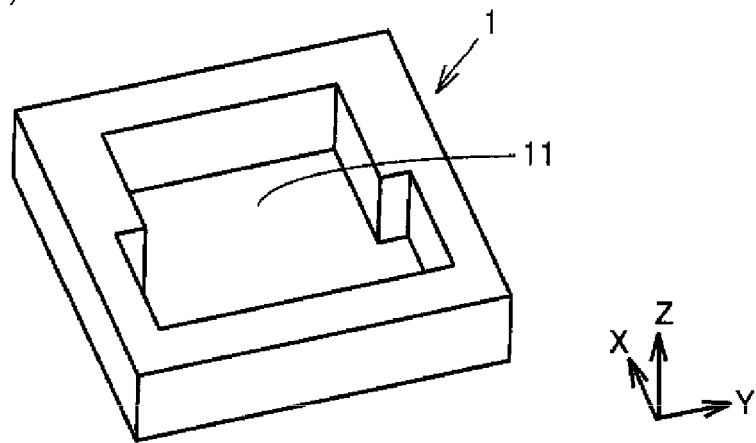
FIG. 19(a) is a perspective view illustrating a void in an example of the flat-plate periodic structure according to the present invention in which the void has a convex shape obtained by centrally projecting one side of a rectangle.
Figure 19B:
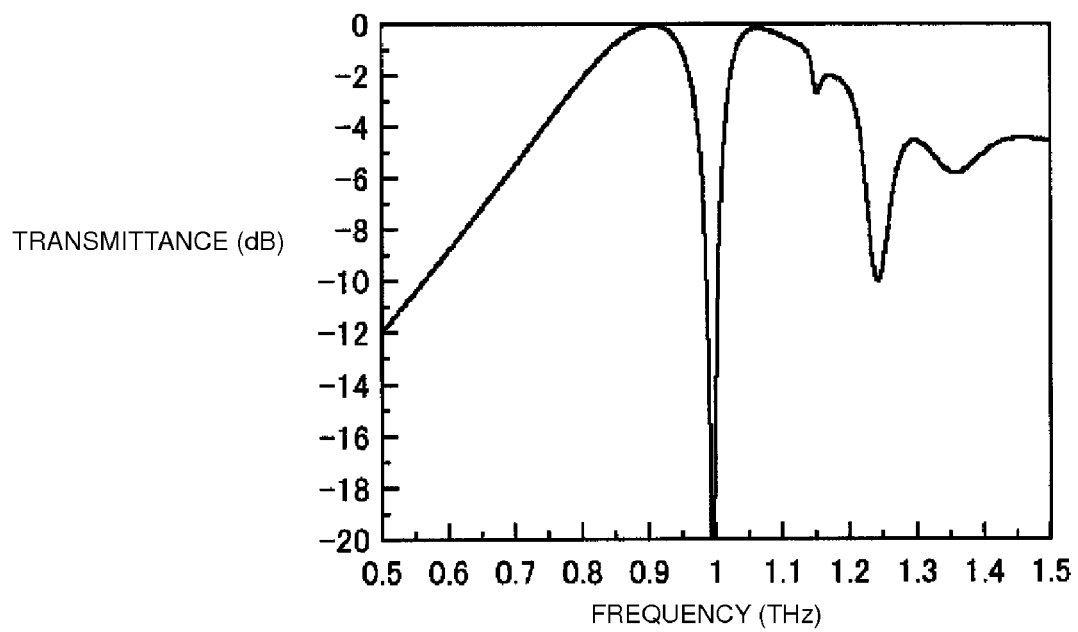
FIG. 19(b) depicts the calculation result of a frequency characteristic of transmittance [dB] with the periodic structure illustrated in FIG. 19(a).
Figure 20A:
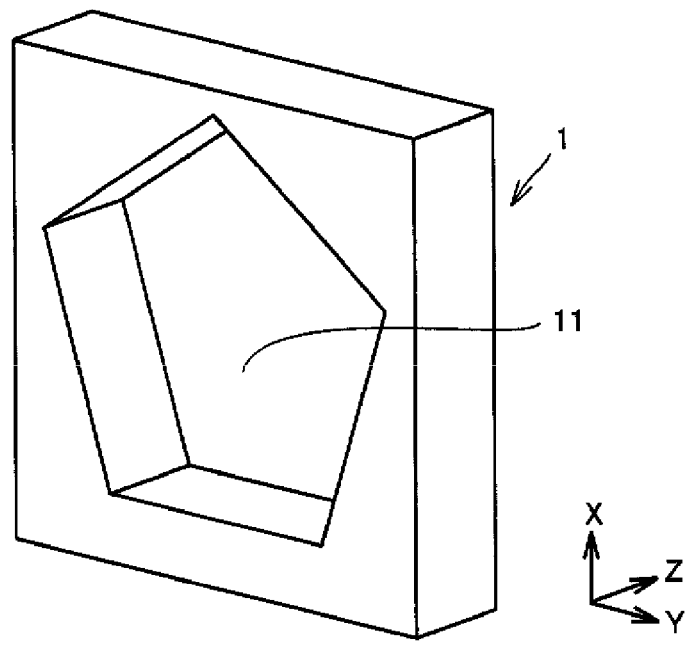
FIG. 20(a) is a perspective view illustrating a void in an example of the flat-plate periodic structure according to the present invention in which the void has a regular pentagonal shape.
Figure 20B:
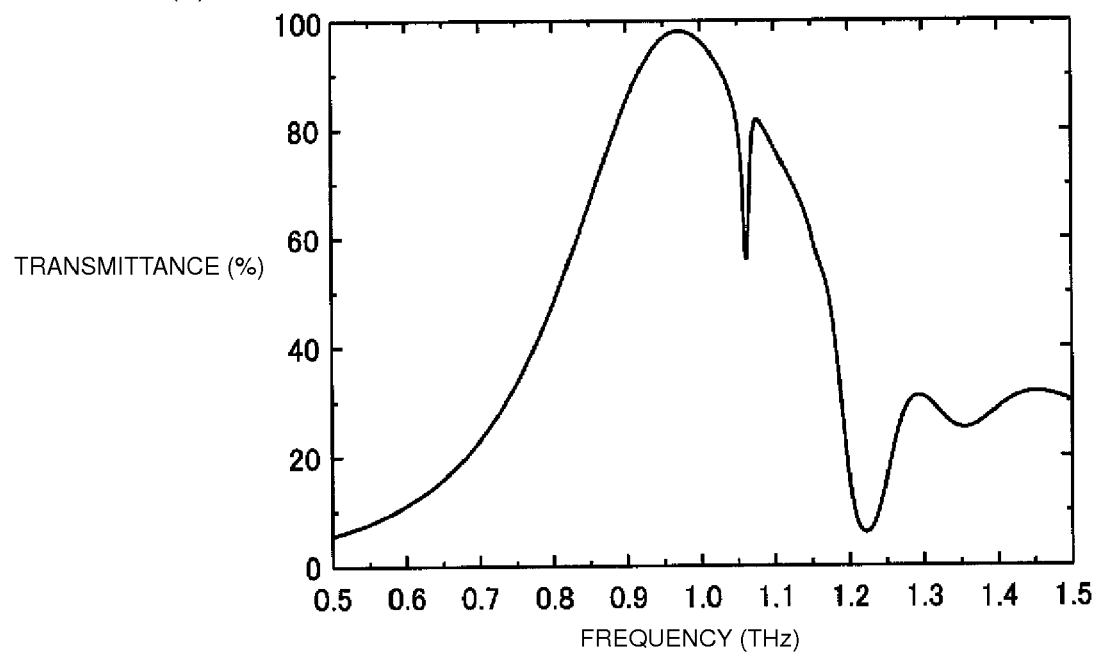
FIG. 20(b) depicts the calculation result of a frequency characteristic of transmittance [%] with the periodic structure illustrated in FIG. 20(a).
Figure 21A:
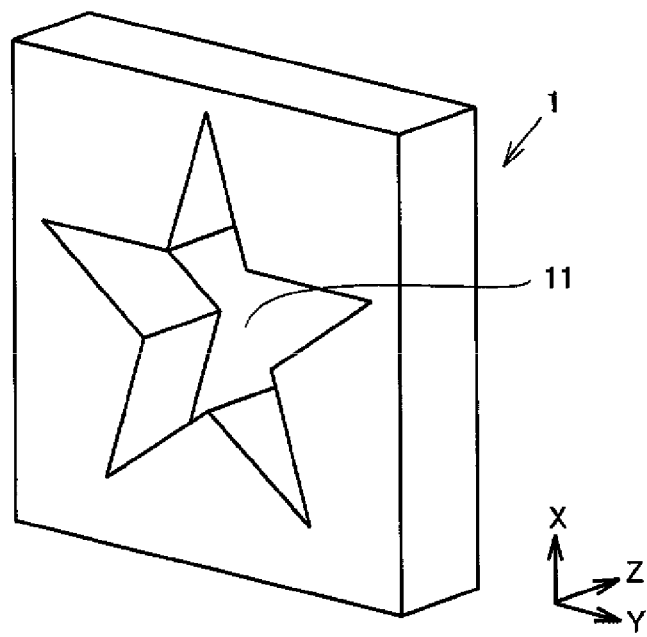
FIG. 21(a) is a perspective view illustrating a void in an example of the flat-plate periodic structure according to the present invention in which the void has a star-like shape.
Figure 21B:
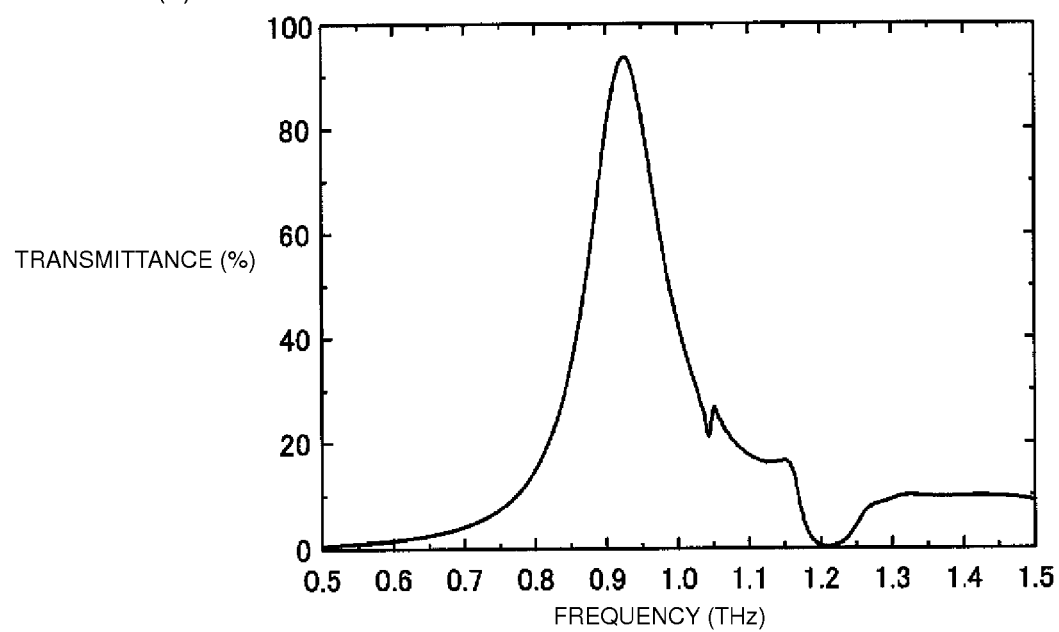
FIG. 21(b) depicts the calculation result of a frequency characteristic of transmittance [%] with the periodic structure illustrated in FIG. 21(a).

[Comparison between Simulated Calculation and Actual Measurement on Periodic Structure Illustrated in FIG. 18(a)]

Figure 25:
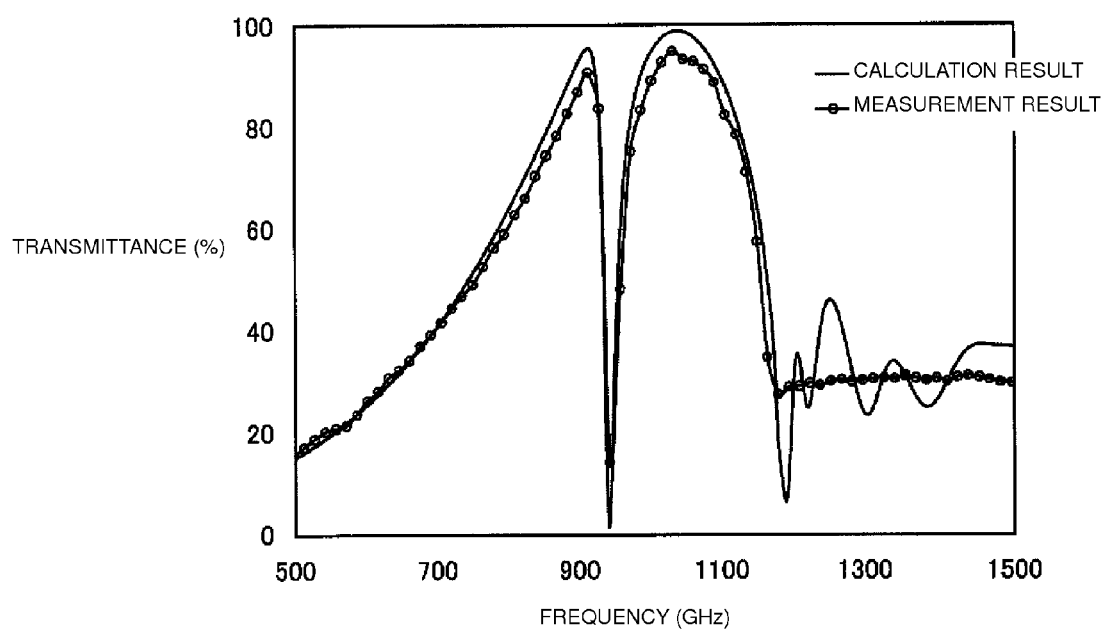
FIG. 25 depicts transmittance spectra obtained with actual measurement and simulation calculation on the structure illustrated in FIG. 18(a).

The periodic structure 1 of the present invention, illustrated in FIG. 18(a), was fabricated in the same manner as that described above in [Actual Measurement on Periodic Structure Illustrated in FIG. 6(a)] relating to EXAMPLE 1, and the frequency characteristic was actually measured. Further, simulated calculation on the periodic structure 1 of the present invention, illustrated in FIG. 18(a), was executed in the same manner as that described above in [Simulated Calculations on Periodic Structures Illustrated in FIGS. 6(a) to 11(a)] relating to EXAMPLE 1. However, the unit of transmittance was set to %. FIG. 25 depicts the results of both the actual measurement and the simulated calculation.

As seen from the results depicted in FIG. 25, the shapes of the dip waveforms are substantially matched with each other between a transmittance spectrum obtained from the actually measured values and a transmittance spectrum obtained with the simulated calculation. In other words, it is understood that, as with the result of the simulated calculation, the dip waveform attributable to the TE11 mode-like resonance is generated by applying the electromagnetic wave to the periodic structure 1, illustrated in FIG. 18(a), from the direction perpendicular to the principal surface of the flat-plate periodic structure.

Further, as seen from comparing the results of the frequency characteristics depicted in FIG. 25 and depicted in FIG. 16 for the related art, the dip waveform appearing in FIG. 25 with the measuring method according to the present invention has a narrower band width and a sharper shape than those of the dip waveform appearing in FIG. 16 with the related-art measuring method, and an increase of measurement sensitivity can be achieved as in EXAMPLE 1 described above.

Example 3

Figure 26A:
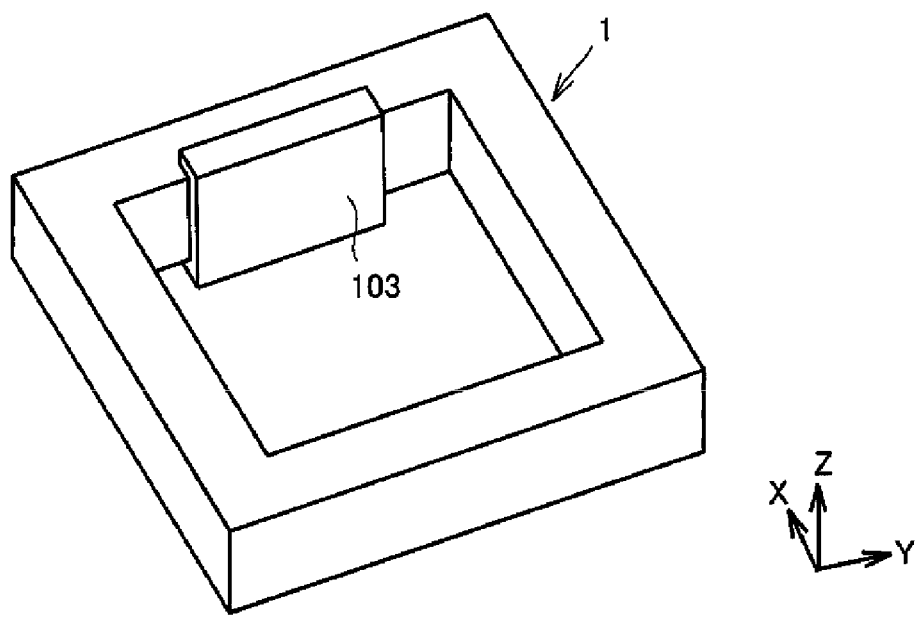
FIG. 26(a) is a perspective view illustrating a void in still another example of the flat-plate periodic structure according to the present invention.

EXAMPLE 3 represents the case where a substance (dielectric) differing from the periodic structure is attached to only a partial region of a portion defining a void of a flat-plate periodic structure (made of Cu). FIG. 26(a) illustrates a flat-plate periodic structure 1 in which a dielectric 103 is attached near a central region of one of side surfaces defining the void.

Figure 26B:
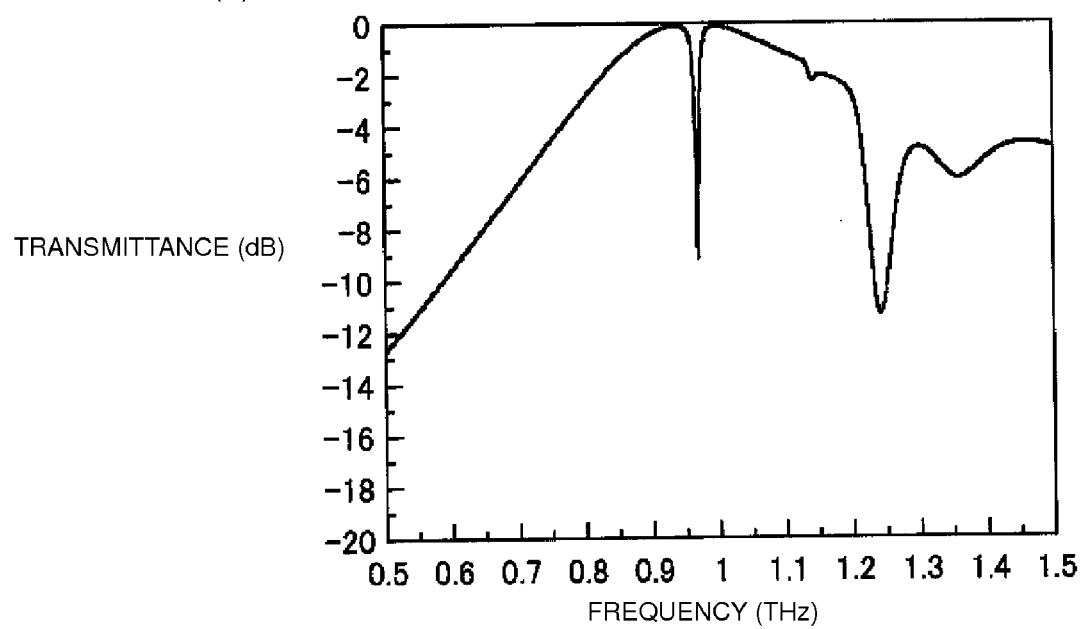
FIG. 26(b) depicts the calculation result of a frequency characteristic of transmittance [dB] with the periodic structure illustrated in FIG. 26(a).

FIG. 26(b) depicts the frequency characteristic of transmittance [dB] calculated for the flat-plate periodic structure 1, illustrated in FIG. 26(a), on the same conditions as those in the electromagnetic simulation in EXAMPLE 1. As seen from the calculation result, the dip waveform attributable to the TE11 mode-like resonance is generated by attaching a substance to the partial region of the portion defining the void of the periodic structure such that two spaces of the void divided by the above-mentioned imaginary plane have different shapes from each other.

To maximize the influence of the dielectric, in EXAMPLE 3, the dielectric is arranged near a central region of one side of a square void in which the electric field intensity is maximized when the TE11 mode-like resonance is generated in the square void (see FIG. 5(a)). When the void shape is changed, the dielectric is preferably arranged, in a similar manner to that described above, at a position where the electric field intensity is relatively increased when the TE11 mode-like resonance is generated in the void having the changed shape.

Further, while EXAMPLE 3 employs the structure in which the voids penetrating through the flat-plate structure are periodically arrayed in a square lattice pattern in the planar direction of the principal surface of the flat-plate structure, similar advantageous effects can be obtained even in a periodic structure having voids arrayed in a triangular lattice pattern insofar as the void has the shape satisfying the above-described conditions.

While EXAMPLE 3 represents the case where a dielectric is used as the substance attached to the void of the periodic structure, similar advantageous effects can also be obtained by using other substances, such as a semiconductor, a magnetic body, and a resistor.

Example 4

EXAMPLE 4 represents the case where a specimen is attached to only a partial region of a portion defining a void of a periodic structure.

Figure 27A:
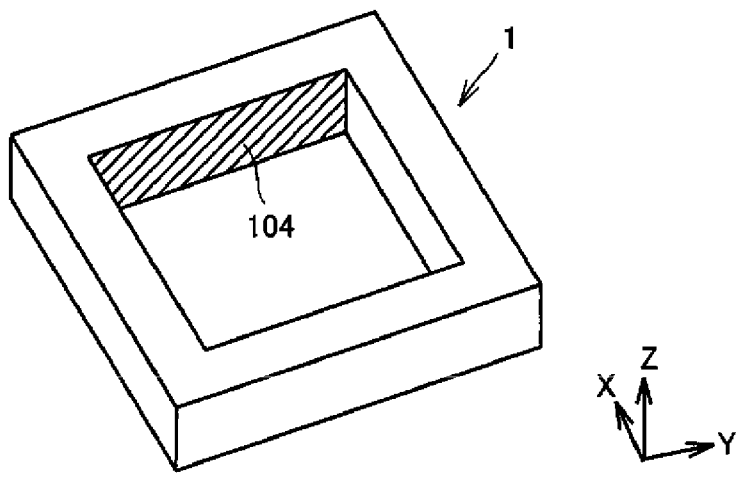
FIG. 27(a) is a perspective view illustrating a void in still another example of the flat-plate periodic structure according to the present invention.

EXAMPLE 4 employs a periodic structure in which, as illustrated in FIG. 27(a), an Au electroless plated film 104 is formed on only one of void side surfaces in the periodic structure 1. The periodic structure of EXAMPLE 4 was fabricated by preparing a Ni-made structure in a similar manner to that in EXAMPLE 1 described above, and then by forming the Au electroless plated film 104 on only one of the void side surfaces in the periodic structure 1 with the photolithography, as illustrated in FIG. 27(a). Further, a polymer having thiol group terminals (i.e., a specimen) was fixated to the Au electroless plated film 104 in a similar manner to that in EXAMPLE 1.

Figure 27B:
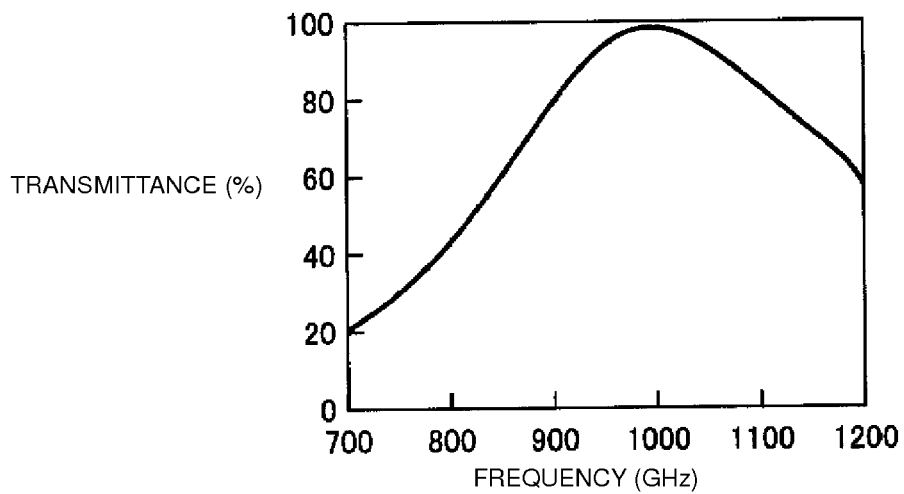
FIG. 27(b) depicts the calculation result of a frequency characteristic of transmittance [dB] with the periodic structure illustrated in FIG. 27(a) before fixation of a polymer.
Figure 27C:
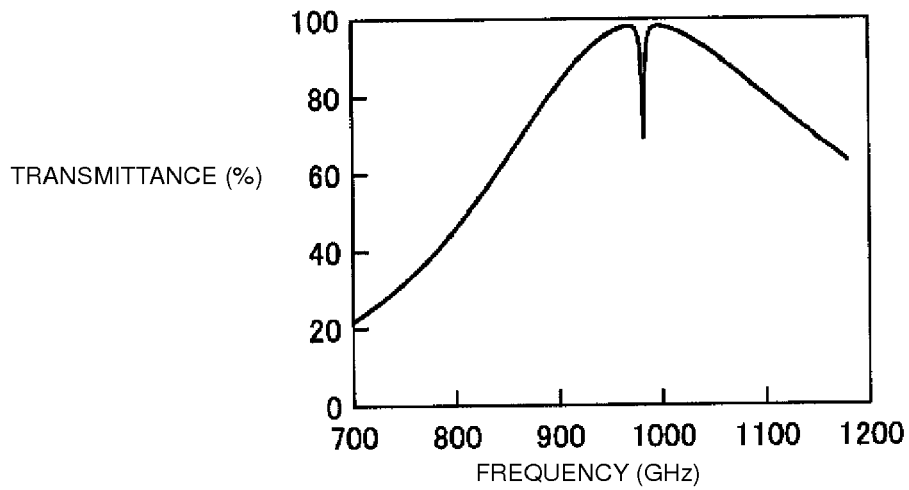
FIG. 27(c) depicts the calculation result of a frequency characteristic of transmittance [dB] with the periodic structure illustrated in FIG. 27(a) after fixation of the polymer.

Frequency characteristics of the transmittance between before and after the fixation of the polymer were actually measured, as in EXAMPLE 1, by using the apparatus configuration illustrated in FIG. 12. FIG. 27(b) depicts the measurement result before the fixation of the polymer, and FIG. 27(c) depicts the measurement result after the fixation of the polymer. As seen from those measurement results, the dip waveform is generated only in the frequency characteristic after the fixation of the polymer, which is illustrated in FIG. 27(c).

Further, as seen from the above discussion, even when the specimen is held at only the partial region of the portion defining the void of the periodic structure, the dip waveform attributable to the TE11 mode-like resonance is generated by applying the electromagnetic wave to the principal surface of the flat-plate periodic structure from the direction perpendicular to the principal surface. Thus, the present invention involves the measuring method including a step of, as described above, holding the specimen at only the partial region of the portion defining the void of the periodic structure.

Moreover, as seen from comparing the frequency characteristic, depicted in FIG. 27(c), with the periodic structure including the polymer (specimen) held thereon and the frequency characteristic, depicted in FIG. 16, for the example using the related-art periodic structure, the dip waveform appearing in FIG. 27(c) according to the present invention has a narrower band width and a sharper shape than those of the dip waveform appearing in FIG. 16 with the related art, and an increase of measurement sensitivity can be achieved as in EXAMPLE 1 described above.

The embodiments and EXAMPLES disclosed here are to be considered as illustrative in all respects, not as restrictive. The scope of the present invention is defined in the appended claims, not by the foregoing description, and it is intended to involve all modifications being equivalent in meaning to the appended claims and falling within the scope defined in the appended claims.

Reference Signs List 1, 9 flat-plate periodic structure, 10a principal surface, 10b side surface, 101 projection, 102 cutout, 103 dielectric, 104 Au electroless plated film, 11, 91 void, 11a, 91a side surface of void, 2 measuring apparatus, 21 irradiation unit, 22 detection unit, 221, 222 detection plane, 23 irradiation control unit, 24 analysis processing unit, 25 display unit, and 3 imaginary plane.

The invention claimed is:

1. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the dip waveform appearing in the frequency characteristic of the forward-scattered electromagnetic wave or the peak waveform appearing in the frequency characteristic of the backward-scattered electromagnetic wave is generated by TE11 mode-like resonance in the periodic structure.

2. The measuring method according to claim 1, wherein the TE11 mode-like resonance is TE110 mode-like resonance.

3. The measuring method according to claim 1, wherein a shape of the at least one void as viewed in the direction perpendicular to the surface of the periodic structure is one of trapezoidal, convex, concave, polygonal, and star-like.

4. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the periodic structure is a flat-plate structure in which at least two voids penetrating through the flat-plate structure in the direction perpendicular to the surface are periodically arrayed in at least one direction on the surface, and
wherein at least one void the at least two voids has a shape that is not minor-symmetric with respect to an imaginary plane perpendicular to a polarizing direction of the linearly-polarized electromagnetic wave.

5. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the periodic structure is a flat-plate structure in which at least two voids penetrating through the flat-plate structure in the direction perpendicular to the surface are periodically arrayed in at least one direction on the surface, and
wherein a projection is provided in a portion defining the at least one void of the periodic structure.

6. The measuring method according to claim 5, wherein the projection is provided at a position in the portion defining the at least one void of the periodic structure at which electric field intensity is relatively intensified when TE11 mode-like resonance is produced.

7. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the periodic structure is a flat-plate structure in which at least two voids penetrating through the flat-plate structure in the direction perpendicular to the surface are periodically arrayed in at least one direction on the surface, and
wherein a cutout is provided in a portion defining the at least one void of the periodic structure.

8. The measuring method according to claim 7, wherein the cutout is provided at a position in the portion defining the at least one void of the periodic structure at which electric field intensity is relatively weakened when TE11 mode-like resonance is produced.

9. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the periodic structure is a flat-plate structure in which at least two voids penetrating through the flat-plate structure in the direction perpendicular to the surface are periodically arrayed in at least one direction on the surface, and
wherein a substance differing from the periodic structure is attached to only a partial region of a portion defining at least one void of the at least two voids of the periodic structure.

10. The measuring method according to claim 9, wherein the substance differing from the periodic structure is selectively held at a position in the portion defining the at least one void of the periodic structure at which electric field intensity is relatively intensified when TE11 mode-like resonance is produced.

11. A measuring method comprising:
applying a linearly-polarized electromagnetic wave to a surface of a periodic structure holding a specimen to be measured, the linearly-polarized electromagnetic wave being applied to the surface of the flat-plate periodic structure from a direction perpendicular to the surface;
detecting an electromagnetic wave scattered forward or backward by the periodic structure; and
measuring characteristics of the specimen based on a change in a dip waveform appearing in a frequency characteristic of the forward-scattered electromagnetic wave or a peak waveform appearing in a frequency characteristic of the backward-scattered electromagnetic wave,
wherein the periodic structure is a flat-plate structure in which at least two voids penetrating through the flat-plate structure in the direction perpendicular to the surface are periodically arrayed in at least one direction on the surface, and
wherein the specimen is held in only a partial region of a portion defining at least one void of the at least two voids of the periodic structure.

12. The measuring method according to claim 11, wherein the specimen is selectively held at the position in the portion defining the at least one void of the periodic structure at which electric field intensity is relatively intensified when TE11 mode-like resonance is produced.

13. A periodic structure comprising:
a flat-plate structure having a surface;
at least two voids penetrating through the flat-plate structure in a direction perpendicular to the surface, the at least two voids being periodically arrayed in at least one direction on the surface of the flat-plate structure, wherein
when the surface of the flat-plate structure is arranged perpendicularly to a propagating direction of an electromagnetic wave, the at least two voids each have a shape that is not mirror-symmetric with respect to an imaginary plane perpendicular to a polarizing direction of the electromagnetic wave.

14. The periodic structure according to claim 13, wherein a projection is provided in a portion of at least one void of the at least two voids.

15. The measuring method according to claim 14, wherein the projection is provided at a position in the portion defining the at least one void at which electric field intensity is relatively intensified when TE11 mode-like resonance is produced.

16. The measuring method according to claim 13, wherein cutout is provided in a respective portion of at least one void of the at least two voids.

17. The measuring method according to claim 16, wherein the cutout is provided at a position in the portion defining the at least one void at which electric field intensity is relatively weakened when TE11 mode-like resonance is produced.

18. The measuring method according to claim 13, wherein a shape of the at least one void as viewed in the direction perpendicular to the surface of the periodic structure is one of trapezoidal, convex, concave, polygonal, and star-like.

* * * * *